(12) United States Patent
Christiansen et al.

(10) Patent No.: US 8,027,030 B2
(45) Date of Patent: Sep. 27, 2011

(54) METHOD AND SYSTEM FOR STANDARDIZING MICROSCOPE INSTRUMENTS

(75) Inventors: Jason Christiansen, Glastonbury, CT (US); Robert Pinard, Andover, MA (US); Maciej P. Zerkowski, Old Lyme, CT (US); Gregory R. Tedeschi, Cromwell, CT (US)

(73) Assignee: HistoRx, Inc., New Haven, CT (US)

( * ) Notice: Subject to any disclaimer, the term of this patent is extended or adjusted under 35 U.S.C. 154(b) by 0 days.

(21) Appl. No.: 13/012,707

(22) Filed: Jan. 24, 2011

(65) Prior Publication Data

US 2011/0116087 A1 May 19, 2011

Related U.S. Application Data

(62) Division of application No. 12/139,370, filed on Jun. 13, 2008, now Pat. No. 7,907,271.

(60) Provisional application No. 60/944,402, filed on Jun. 15, 2007.

(51) Int. Cl.
*G01J 1/40* (2006.01)
*G02B 27/14* (2006.01)

(52) U.S. Cl. ..................................... 356/243.8; 359/634

(58) Field of Classification Search .... 356/237.1–241.6, 356/242.1–243.8, 426–431, 600–640
See application file for complete search history.

(56) References Cited

U.S. PATENT DOCUMENTS

| | | | |
|---|---|---|---|
| 3,958,122 A * | 5/1976 | Jowett et al. | 250/346 |
| 4,480,189 A | 10/1984 | Miyake et al. | |
| 4,557,599 A * | 12/1985 | Zimring | 356/243.1 |
| 4,859,062 A | 8/1989 | Thurn et al. | |
| 4,892,817 A | 1/1990 | Pawlak | |
| 4,902,131 A * | 2/1990 | Yamazaki et al. | 356/336 |
| 4,904,088 A | 2/1990 | Blazek et al. | |

(Continued)

FOREIGN PATENT DOCUMENTS

EP 0 709 667 5/1996

(Continued)

OTHER PUBLICATIONS

A.K. Jain et al, "Data Clustering: A Review", ACM Computing Surveys, vol. 31, No. 3, Sep. 1999, pp. 264-323.

(Continued)

*Primary Examiner* — Gregory J Toatley
*Assistant Examiner* — Jarreas C Underwood
(74) *Attorney, Agent, or Firm* — Gilberto M. Villacorta; Nikhil Palekar; Foley & Lardner LLP

(57) ABSTRACT

Methods and apparatus for standardizing quantitative measurements from a microscope system. The process includes a calibration procedure whereby an image of a calibration slide is obtained through the optics of the microscope system. The calibration slide produces a standard response, which can be used to determine a machine intrinsic factor for the particular system. The machine intrinsic factor can be stored for later reference. In use, images are acquired of a target sample and of the excitation light source. The excitation light source sample is obtained using a calibration instrument configured to sample intensity. The calibration instrument has an associated correction factor to compensate its performance to a universally standardized calibration instrument. The machine intrinsic factor, sampled intensity, and calibration instrument correction factor are usable to compensate a quantitative measurement of the target sample in order to normalize the results for comparison with other microscope systems.

6 Claims, 13 Drawing Sheets

U.S. PATENT DOCUMENTS

| | | | |
|---|---|---|---|
| 4,910,398 A | 3/1990 | Komatsu et al. | |
| 4,912,034 A | 3/1990 | Kalra et al. | |
| 4,927,266 A * | 5/1990 | Sugiura et al. | 356/243.1 |
| 5,015,098 A * | 5/1991 | Berg et al. | 356/402 |
| 5,068,909 A | 11/1991 | Rutherford et al. | |
| 5,070,455 A * | 12/1991 | Singer et al. | 378/6 |
| 5,097,119 A | 3/1992 | Breitmeier | |
| 5,115,673 A | 5/1992 | Kline et al. | |
| 5,126,577 A | 6/1992 | Trent | |
| 5,244,787 A | 9/1993 | Key et al. | |
| 5,254,845 A | 10/1993 | Burgess et al. | |
| 5,309,108 A * | 5/1994 | Maeda et al. | 324/501 |
| 5,422,018 A | 6/1995 | Saunders et al. | |
| 5,427,910 A | 6/1995 | Kamentsky et al. | |
| 5,432,054 A | 7/1995 | Saunders et al. | |
| 5,439,649 A | 8/1995 | Tseung et al. | |
| 5,489,386 A | 2/1996 | Saunders | |
| 5,492,837 A | 2/1996 | Naser-Kolahzadeh et al. | |
| 5,523,207 A | 6/1996 | Kamentsky et al. | |
| 5,561,556 A | 10/1996 | Weissman | |
| 5,578,452 A | 11/1996 | Shi et al. | |
| 5,587,833 A | 12/1996 | Kamentsky | |
| 5,602,674 A | 2/1997 | Weissman et al. | |
| 5,633,945 A | 5/1997 | Kamentsky | |
| 5,672,881 A | 9/1997 | Striepeke et al. | |
| 5,682,567 A | 10/1997 | Spruck et al. | |
| 5,694,212 A | 12/1997 | Weissman | |
| 5,717,198 A * | 2/1998 | Broude et al. | 250/205 |
| 5,731,156 A | 3/1998 | Golbus | |
| 5,784,529 A | 7/1998 | Richmond | |
| 5,880,473 A | 3/1999 | Ginestet | |
| 5,885,840 A | 3/1999 | Kamentsky et al. | |
| 5,889,881 A | 3/1999 | MacAulay et al. | |
| 5,916,750 A | 6/1999 | Iyer et al. | |
| 5,948,359 A | 9/1999 | Kalra et al. | |
| 5,962,234 A | 10/1999 | Golbus | |
| 5,978,497 A | 11/1999 | Lee et al. | |
| 6,002,788 A | 12/1999 | Luther | |
| 6,026,174 A | 2/2000 | Palcic et al. | |
| 6,031,930 A | 2/2000 | Bacus et al. | |
| 6,049,220 A * | 4/2000 | Borden et al. | 324/754.23 |
| 6,052,190 A | 4/2000 | Sekowski et al. | |
| 6,087,134 A | 7/2000 | Saunders | |
| 6,101,265 A | 8/2000 | Bacus et al. | |
| 6,130,323 A | 10/2000 | Su et al. | |
| 6,134,354 A | 10/2000 | Lee et al. | |
| 6,137,899 A | 10/2000 | Lee et al. | |
| 6,151,405 A | 11/2000 | Douglass et al. | |
| 6,165,739 A | 12/2000 | Clatch | |
| 6,169,816 B1 | 1/2001 | Ravkin | |
| 6,215,892 B1 | 4/2001 | Douglass et al. | |
| 6,221,607 B1 | 4/2001 | Tsipouras et al. | |
| 6,225,636 B1 | 5/2001 | Ginestet | |
| 6,226,392 B1 | 5/2001 | Bacus et al. | |
| 6,239,868 B1 * | 5/2001 | Jung et al. | 356/73 |
| 6,259,807 B1 | 7/2001 | Ravkin | |
| 6,270,971 B1 | 8/2001 | Ferguson-Smith et al. | |
| 6,272,235 B1 | 8/2001 | Bacus et al. | |
| 6,309,601 B1 * | 10/2001 | Juncosa et al. | 422/68.1 |
| 6,330,349 B1 | 12/2001 | Hays et al. | |
| 6,396,941 B1 | 5/2002 | Bacus et al. | |
| 6,404,906 B2 | 6/2002 | Bacus et al. | |
| 6,404,916 B1 | 6/2002 | De La Torre-Bueno | |
| 6,408,048 B2 * | 6/2002 | Opsal et al. | 378/89 |
| 6,418,236 B1 | 7/2002 | Ellis et al. | |
| 6,445,817 B1 | 9/2002 | De La Torre-Bueno | |
| 6,451,551 B1 | 9/2002 | Zhan et al. | |
| 6,466,690 B2 | 10/2002 | Bacus et al. | |
| 6,493,460 B1 | 12/2002 | MacAulay et al. | |
| 6,495,106 B1 | 12/2002 | Kalra et al. | |
| 6,518,554 B1 | 2/2003 | Zhang | |
| 6,522,744 B1 | 2/2003 | Chiang | |
| 6,524,798 B1 | 2/2003 | Goldbard et al. | |
| 6,546,123 B1 | 4/2003 | McLaren et al. | |
| 6,553,135 B1 | 4/2003 | Douglass et al. | |
| 6,589,792 B1 | 7/2003 | Malachowski | |
| 6,631,203 B2 | 10/2003 | Ellis et al. | |
| 6,632,598 B1 | 10/2003 | Zhang et al. | |
| 6,633,662 B2 | 10/2003 | Ravkin | |
| 6,648,506 B2 * | 11/2003 | McGrath et al. | 374/161 |
| 6,671,393 B2 | 12/2003 | Hays et al. | |
| 6,674,058 B1 | 1/2004 | Miller | |
| 6,674,896 B1 | 1/2004 | Torre-Bueno | |
| 6,697,509 B2 | 2/2004 | De La Torre-Bueno | |
| 6,718,053 B1 | 4/2004 | Ellis et al. | |
| 6,746,873 B1 | 6/2004 | Buchanan et al. | |
| 6,777,194 B1 | 8/2004 | Gerdes et al. | |
| 6,778,714 B1 * | 8/2004 | Kipman et al. | 382/313 |
| 6,780,377 B2 | 8/2004 | Hall et al. | |
| 6,800,249 B2 | 10/2004 | De La Torre-Bueno | |
| 6,816,625 B2 * | 11/2004 | Lewis et al. | 382/275 |
| 6,852,986 B1 * | 2/2005 | Lee et al. | 250/458.1 |
| 6,876,760 B1 | 4/2005 | Vaisberg et al. | |
| 6,881,580 B2 | 4/2005 | Hall et al. | |
| 6,882,873 B2 | 4/2005 | Samuels et al. | |
| 6,900,426 B2 | 5/2005 | Zhang | |
| 6,920,239 B2 | 7/2005 | Douglass et al. | |
| 6,947,583 B2 | 9/2005 | Ellis et al. | |
| 7,006,680 B2 | 2/2006 | Gulati | |
| 7,024,316 B1 | 4/2006 | Ellison et al. | |
| 7,064,829 B2 | 6/2006 | Li et al. | |
| 7,070,951 B2 | 7/2006 | Zhang et al. | |
| 7,084,386 B2 | 8/2006 | Bernardini et al. | |
| 7,113,205 B2 * | 9/2006 | Cappellaro | 348/218.1 |
| 7,116,354 B2 * | 10/2006 | Rice et al. | 348/187 |
| 7,123,756 B2 * | 10/2006 | Hakamata et al. | 382/128 |
| 7,129,053 B1 | 10/2006 | Reiter et al. | |
| 7,133,543 B2 | 11/2006 | Verwoerd et al. | |
| 7,133,545 B2 | 11/2006 | Douglass et al. | |
| 7,146,062 B2 | 12/2006 | De La Torre-Bueno et al. | |
| 7,171,054 B2 | 1/2007 | Fiete et al. | |
| 7,177,454 B2 | 2/2007 | McLaren et al. | |
| 7,189,576 B2 * | 3/2007 | Fukuoka et al. | 436/170 |
| 7,190,818 B2 | 3/2007 | Ellis et al. | |
| 7,199,360 B1 * | 4/2007 | Montagu | 250/252.1 |
| 7,205,154 B2 * | 4/2007 | Corson | 436/164 |
| 7,212,660 B2 | 5/2007 | Wetzel et | |
| 7,219,016 B2 | 5/2007 | Rimm et al. | |
| 7,224,470 B2 | 5/2007 | Vaux et al. | |
| 7,224,839 B2 | 5/2007 | Zeineh | |
| 7,229,774 B2 | 6/2007 | Chinnaiyan et al. | |
| 7,233,340 B2 | 6/2007 | Hughes et al. | |
| 7,236,623 B2 | 6/2007 | Chapoulaud et al. | |
| 7,257,267 B2 | 8/2007 | Recht | |
| 7,272,252 B2 | 9/2007 | De La Torre-Bueno et al. | |
| 7,316,907 B2 | 1/2008 | Yu et al. | |
| 7,330,250 B2 * | 2/2008 | Gip et al. | 356/239.2 |
| 7,332,290 B2 | 2/2008 | Rubin et al. | |
| 7,369,696 B2 | 5/2008 | Arini et al. | |
| 7,376,256 B2 | 5/2008 | Kirsch et al. | |
| 7,383,134 B2 | 6/2008 | Piper et al. | |
| 7,474,847 B2 | 1/2009 | Nikkanen et al. | |
| 7,639,350 B2 | 12/2009 | Noguchi et al. | |
| 2002/0141049 A1 | 10/2002 | Masuyama | |
| 2003/0138827 A1 | 7/2003 | Kononen et al. | |
| 2003/0215936 A1 | 11/2003 | Kallioniemi et al. | |
| 2004/0056966 A1 * | 3/2004 | Schechner et al. | 348/229.1 |
| 2004/0085475 A1 | 5/2004 | Skow et al. | |
| 2004/0215087 A1 | 10/2004 | Genero et al. | |
| 2005/0037406 A1 | 2/2005 | De La Torre-Bueno et al. | |
| 2005/0105787 A1 | 5/2005 | Gulati | |
| 2005/0136509 A1 | 6/2005 | Gholap et al. | |
| 2005/0142579 A1 | 6/2005 | Sugiyama et al. | |
| 2005/0266395 A1 | 12/2005 | Gholap et al. | |
| 2006/0001765 A1 | 1/2006 | Suda | |
| 2006/0014238 A1 | 1/2006 | Gholap et al. | |
| 2006/0015262 A1 | 1/2006 | Gholap et al. | |
| 2006/0063190 A1 | 3/2006 | Fischer et al. | |
| 2006/0078926 A1 | 4/2006 | Marcelpoil et al. | |
| 2006/0127946 A1 | 6/2006 | Montagu et al. | |
| 2006/0160169 A1 | 7/2006 | Marcotte et al. | |
| 2006/0166253 A1 | 7/2006 | Kononen et al. | |
| 2006/0188140 A1 | 8/2006 | Gholap et al. | |
| 2006/0211017 A1 | 9/2006 | Chinnaiyan et al. | |
| 2006/0239533 A1 | 10/2006 | Tafas et al. | |
| 2006/0275844 A1 | 12/2006 | Linke et al. | |
| 2007/0114388 A1 | 5/2007 | Ogawa et al. | |

| | | | |
|---|---|---|---|
| 2007/0154958 | A1 | 7/2007 | Hamann et al. |
| 2007/0207489 | A1 | 9/2007 | Pestano et al. |
| 2008/0013816 | A1 | 1/2008 | Rimm et al. |
| 2008/0026415 | A1 | 1/2008 | Rimm et al. |
| 2008/0118437 | A1 | 5/2008 | Pienta et al. |
| 2008/0153098 | A1 | 6/2008 | Rimm et al. |
| 2008/0153877 | A1 | 6/2008 | Adimoolam et al. |
| 2009/0167850 | A1 | 7/2009 | Bruno et al. |

FOREIGN PATENT DOCUMENTS

| | | | |
|---|---|---|---|
| EP | 0 549 905 | | 4/1999 |
| EP | 0 977 981 | A1 | 2/2000 |
| EP | 0 720 114 | | 1/2001 |
| EP | 1 065 496 | | 3/2001 |
| EP | 1 202 563 | | 5/2002 |
| EP | 1 251 179 | | 10/2002 |
| EP | 1 300 713 | | 4/2003 |
| EP | 1 329 513 | | 7/2003 |
| EP | 1 347 285 | A1 | 9/2003 |
| EP | 1 779 088 | | 2/2006 |
| EP | 1 502 098 | | 9/2008 |
| GB | 2 305 723 | | 4/1997 |
| GB | 2 395 263 | | 5/2004 |
| GB | 2 396 406 | | 6/2004 |
| GB | 2 406 908 | | 4/2005 |
| GB | 2 423 150 | | 8/2006 |
| GB | 2 430 026 | | 3/2007 |
| JP | 02-232550 | | 9/1990 |
| JP | 04-315119 | | 11/1992 |
| JP | 05-249102 | | 9/1993 |
| JP | 07-030753 | | 1/1995 |
| JP | 11-183381 | | 7/1999 |
| JP | 2001-211896 | | 8/2001 |
| JP | 2003-284713 | | 10/2003 |
| JP | 2003-294734 | | 10/2003 |
| JP | 2004-354346 | | 12/2004 |
| JP | 2005-070537 | | 3/2005 |
| JP | 2006-194711 | | 7/2006 |
| JP | 2007-127485 | | 5/2007 |
| JP | 2007-232631 | | 9/2007 |
| JP | 2007-271484 | | 10/2007 |
| JP | 2007-278984 | | 10/2007 |
| WO | WO-95/34050 | | 12/1995 |
| WO | WO-96/09604 | | 3/1996 |
| WO | WO-96/09605 | | 3/1996 |
| WO | WO-96/23898 | | 8/1996 |
| WO | WO-98/07022 | | 2/1998 |
| WO | WO-99/30278 | | 6/1999 |
| WO | WO-00/64147 | | 10/2000 |
| WO | WO-00/79326 | A1 | 12/2000 |
| WO | WO-02/056584 | | 7/2002 |
| WO | WO-02/067188 | | 8/2002 |
| WO | WO-02/086498 | | 10/2002 |
| WO | WO-02/099429 | | 12/2002 |
| WO | WO-03/008963 | | 1/2003 |
| WO | WO-03/056343 | | 7/2003 |
| WO | WO-03/093810 | | 11/2003 |
| WO | WO-03/097850 | A1 | 11/2003 |
| WO | WO-03/098522 | | 11/2003 |
| WO | WO-2004/025569 | | 3/2004 |
| WO | WO-2004/059288 | | 7/2004 |
| WO | WO-2005/027015 | | 3/2005 |
| WO | WO-2005/033706 | | 4/2005 |
| WO | WO-2005/045734 | | 5/2005 |
| WO | WO-2005/076197 | | 8/2005 |
| WO | WO 2005/076216 | | 8/2005 |
| WO | WO-2005/077263 | | 8/2005 |
| WO | WO-2005/096225 | | 10/2005 |
| WO | WO-2005/114578 | | 12/2005 |
| WO | WO-2006/036726 | | 4/2006 |
| WO | WO-2006/036788 | | 4/2006 |
| WO | WO-2006/039396 | | 4/2006 |
| WO | WO-2006/054991 | | 5/2006 |
| WO | WO-2006/083969 | A2 | 8/2006 |
| WO | WO-2006/102233 | | 9/2006 |
| WO | WO-2006/105519 | | 10/2006 |
| WO | WO-2006/122251 | | 11/2006 |
| WO | WO-2006/133325 | A2 | 12/2006 |
| WO | WO-2007/024264 | | 3/2007 |
| WO | WO-2007/133465 | | 11/2007 |
| WO | WO-2008/012771 | | 1/2008 |

OTHER PUBLICATIONS

A.K. Katoh et al., "Immunoperoxidase Staining for Estrogen and Progesterone Receptors in Archival Formalin Fixed, Paraffin Embedded Breast Carcinomas after Microwave Antigen Retrieval," Biotechnic & Histochemistry, vol. 72, No. 6, pp. 291-298, Nov. 1997.

A.R. Leitch, In Situ Hybridization: A Practical Guide, Oxford BIOS Scientific Publishers, Microscopy Handbooks (1994).

Aaron J. Berger et al., "Automated Quantitative Analysis of HDM2 Expression in Malignant Melanoma Shows Associaion with Early-Stage Disease and Improved Outcome," Cancer Research, vol. 64, Dec. 2004, pp. 8767-8772.

Anthony McCabe et al., "Automated Quantitative Analysis (AQUA) of In Situ Protein Expression, Antibody Concentration, and Prognosis," Journal of the National Cancer Institute, vol. 97, No. 24, pp. 1808-1815, Dec. 21, 2005.

Chen, et al., "Ratio-Based Decisions and the Quantitative Analysis of cDNA Microarray Images," Journal of Biomedical Optics, SPIE, Bellingham, WA, vol. 2, No. 4, Oct. 1, 1997, pp. 364-374.

Communication mailed Apr. 28, 2010 in European Appln No. 08754418.5.

D.R.J. Snead et al., "Methodology of Immunohistological Detection of Oestrogen Receptor in Human Breast Carcinoma in Formalin-Fixed, Paraffin-Embedded Tissue: A Comparison with Frozen Section Methodology," Histopathology, vol. 23, pp. 233-238, 1993.

David J. Miller et al., "Emergent Unsupervised Clustering Paradigms with Potential Application to Bioinformatics," Frontiers in Bioscience, vol. 13, Jan. 2008, pp. 677-690.

David L. Rimm, MD PhD., et al., "Tissue Microarray: A New Technology for Amplification of Tissue Resources," The Cancer Journal, vol. 7, No. 1, Jan./Feb. 2001, pp. 24-31.

Duggan, et al., "Expression Profiling Using cDNA Microarrays," Nature Genetics, Nature Publishing Group, New York, vol. 21, No. Suppl., Jan. 1, 1999, pp. 10-14.

Feng, et al., "Adaptive Kurtosis Optimization Autofocus Algorithm," Journal of Electronics, vol. 23, No. 4, Jul. 2006, pp. 532-534.

Gina G. Chung et al., "Tissue Microarray Analysis of B-Catenin in Colorectal Cancer Shows Nuclear Phospho-B-catenin is Associated with a Better Prognosis," Clinical Cancer Research, vol. 7, pp. 4013-2010, Dec. 2001.

J. Sambrook, E. F. Fritsch, and T. Maniatis. (1989) Molecular cloning, a laboratory manual. Cold Spring Harbor Laboratory Press, Cold Spring Harbor, N.Y., 30 pages.

Jacqueline F. MfGinty et al., "Double Immunostaining Reveals Distinctions Among Opioid Peptidergic Neurons in the Medical Basal Hypothalamus," Brain Research, vol. 278, pp. 145-153, 1983, Elsevier.

Jules M. Elias, PhD., Immunoshistopathology A Practical Approach to Diagnosis,: American Society of Clinical Pathologists, Chicago, 1990.

Kevin A. Roth et al., "Enzyme-based Antigen Localization and Quantitation in Cell and Tissue Samples (Midwestern Assay)," The Journal of Histochemistry & Cytochemistry, vol. 45(12), pp. 1629-1641, 1997.

Kononen, Juha et al., "Tissue Microarrays for High-Throughput Molecular Profiling of Tumor Specimens," Nature Medicine, vol. 4, No. 7, Jul. 1998, pp. 844-847.

M. Cregger et al., "Immunohistochemistry and Quantative Analysis of Protein Expression," Arch Pathol Lab Med, vol. 130, Jul. 2006, pp. 1026-1030.

Marisa Dolled-Filhart et al., "Classification of Breast Cancer Using Genetic Algorithms and Tissue Microarrays," Clin Cancer Research, vol. 12(21), pp. 6459-6468, Nov. 1, 2006, www.aacrjournals.org.

Marisa Dolled-Filhart et al., "Tissue Microarray Analysis of Signal Transducers and Activators of Transcription 3 (Stat3) and Phospho-Stat3 (Tyr705) in Node-negative Breast Cancer Shows Nuclear Localization is Associated with a Better Prognosis," Clinical Cancer Research, vol. 9, Feb. 2003, pp. 594-600.

Notice of Allowance mailed Dec. 8, 2010 in U.S. Appl. No. 12/139,370.
Notice of Allowance mailed Feb. 18, 2011 in U.S. Appl. No. 12/201,753.

Office Action mailed May 12, 2010 in U.S. Appl. No. 12/139,370.
Office Action mailed Nov. 10, 2010 in U.S. Appl. No. 12/201,753.

* cited by examiner

METHOD AND SYSTEM FOR STANDARDIZING MICROSCOPE INSTRUMENTS

CROSS-REFERENCE TO RELATED PATENT APPLICATIONS

This application is a Divisional of U.S. application Ser. No. 12/139,370, filed Jun. 13, 2008, which claims the benefit of U.S. Provisional Patent Application No. 60/944,402, filed Jun. 15, 2007, both of which are incorporated herein by reference in their entirety.

FIELD

The present invention relates generally to the field of microscopy and more particularly to standardizing quantitative analytical results obtained from the same or different microscope systems to allow comparisons therebetween.

BACKGROUND

As microscopy platforms become quantitative, a simple method and hardware combination to allow standardization between these platforms needs to be developed. For example, in fluorescent microscopy applications, there are products currently available to measure fluorescence intensity for a system (i.e., fluorescent microspheres, fluorescent targets), but they do not provide an overall efficiency factor that is related to variations in the overall construction of a microscope platform, or variations in the light source independent of sample variations.

SUMMARY

The systems and processes described herein provide normalization factors for a given optical microscopy system that can be used to standardize and scale quantitative measurement results. Standardization allows for comparison of quantitative results obtained from different instruments, the results from each instrument having undergone the same standardization. Also, as an extension of this, the same hardware that contributes to the instrument efficiency normalization factors can be used to measure variations in light source intensity during an experiment in which several exposures are taken on a single platform over time.

In one aspect, the invention relates to a process for standardizing a quantitative measurement of target sample data imaged by an optical system. The optical system has an excitation light source, an optics portion, an image capture portion, and a data storage portion. The various portions of the optical system are cooperatively arranged for obtaining an image of the target sample. A light source correction factor is obtained for the excitation light source. The light source correction factor is applied to the target sample data, thereby obtaining a target sample data standardized with regard to light intensity variability. A quantitative measure of the standardized target sample data is determined.

In another aspect, the invention relates to a calibration instrument for sampling illumination of an excitation light source of a microscopy system. The system includes a calibration surface positioned along an optical path. The calibration surface substantially uniformly scatters illumination from the excitation light source toward a detection portion of the microscopy system. In some embodiments, the system includes a dichromatic mirror positioned to reflect illumination from the excitation light source along an optical path through an objective toward a target sample and to transmit at least a portion of illumination from the target sample toward a detection portion of the microscopy system. In such embodiments, the calibration surface is positioned to temporarily block the optical path between the dichromatic mirror and the objective during calibration and scatter a substantial portion of the reflected excitation light through the dichromatic mirror toward the detector.

In another aspect, the invention relates to a process for obtaining a quantitative standardized target sample data measurement from an optical system. The optical system has an excitation light source, an optics portion, a detection portion, and a data storage portion, cooperatively arranged for obtaining target sample data. An optical system intrinsic factor is obtained for the optical system. The optical system intrinsic factor is applied to the target sample data, thereby obtaining a target sample data measurement standardized with regards to intrinsic optical factors.

In another aspect, the invention relates to a process for obtaining a standardized measurement from a microscope system having an excitation light source, an optics portion, and a detection portion cooperatively arranged for obtaining an image of a target sample. The process includes illuminating with the excitation light source a calibration sample configured to produce a standard response to the illumination. A calibration sample image of the illuminated calibration sample obtained through the optics portion is captured with the detection portion. A calibration instrument configured to direct a sample portion of illumination from the excitation light source toward the detector is illuminated with excitation light source. An excitation light source sample image of the directed sample portion is captured with the detection portion, and a machine intrinsic factor for correcting variations along the optical path is determined from the calibration sample image and the excitation light source sample image. The machine intrinsic factor is usable to compensate a target sample image for intrinsic variations of the microscope system.

In another aspect, the invention relates to a computer-usable medium having computer readable instructions stored thereon for execution by a processor performing one or more of the processes described herein.

In another aspect, the invention relates to electromagnetic signal carrying computer-readable instructions for obtaining a standardized measurement from a microscope system having an excitation light source, an optics portion, and a detection portion cooperatively arranged for obtaining an image of a target sample, in which the instructions perform the process described above.

In another aspect, the invention relates to a microscope system providing a standardized measurement, including means for illuminating with the excitation light source a calibration sample configured to produce a standard response to the illumination, means for capturing with the detection portion a calibration sample image of the illuminated calibration sample obtained through the optics portion, means for illuminating with excitation light source a calibration instrument configured to direct a sample portion of illumination from the excitation light source toward the detector, and means for capturing with the detection portion an excitation light source sample image of the directed sample portion. The system also includes means for determining from the calibration sample image and the excitation light source sample image a machine intrinsic factor for correcting variations along the optical path, the machine intrinsic factor usable to compensate a target sample image for intrinsic variations of the microscope system.

In another aspect, the invention relates to a system for compensating for intensity measurements of a target sample in a microscope system. The system includes a stage for supporting the target sample, an excitation light source for illuminating the stage supported target sample, a detection portion for detecting an image of the illuminated target sample, and a calibration instrument configured for temporary insertion along an optical axis between the excitation light source and the detection portion to redirect a sample portion of the excitation light source to the detection portion during calibration. Beneficially, the calibration instrument allows for redirection of the excitation light source without disturbing the staged target sample. The system also includes an analyzer in communication with the detection portion for determining an intensity correction factor determined from the redirected sample portion. The intensity correction factor is usable to adjust detected images of the illuminated target sample to compensate for excitation light source variations.

In yet another aspect, the invention relates to a process for correcting intensity fluctuations in a fluorescence microscope system having an excitation light source, an optics portion, and a detection portion cooperatively arranged for obtaining an image of a target sample. The process includes inserting a calibration element in an optical path between an objective and the detection portion. The calibration element includes a dichromatic mirror and a calibration surface. The mirror is adapted to reflect light from the excitation light source toward the calibration surface and to transmit a sample of excitation light returned from the calibration surface toward the detector. An intensity variation of the excitation light source is determined from the sample of excitation light returned from the calibration surface. The calibration element is replaced with a filter set adapted to reflect a selected spectrum of the excitation light source toward the target sample. A selected spectrum of illumination is transmitted from the target sample toward the detector portion. Selected emission light spectrum is detected from the target sample and the detected emission light spectrum from the target sample is corrected using the determined intensity variation of the excitation light source.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
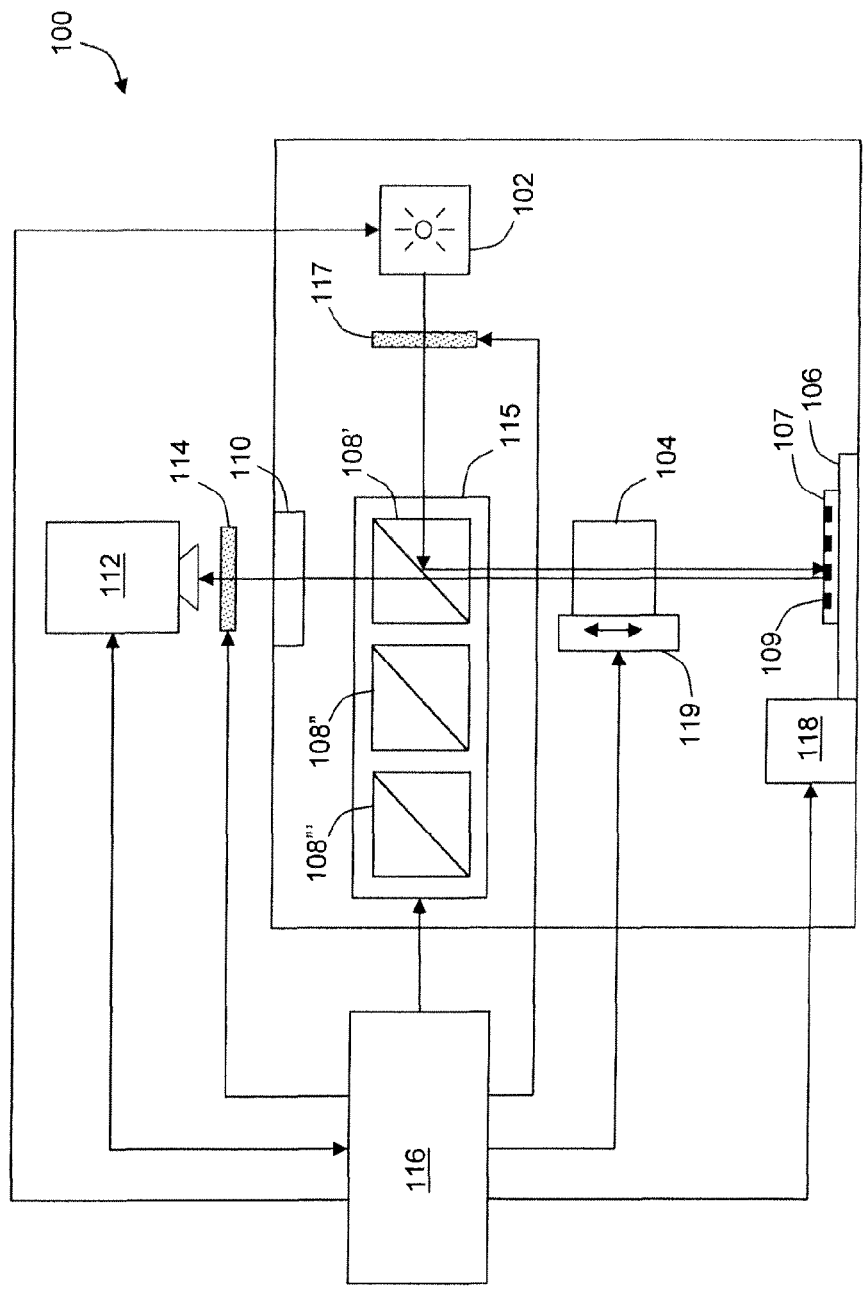
FIG. 1 shows a block diagram of an exemplary microscope system.

Systems and processes are described herein for obtaining standardized quantitative analytical results from a system including optical components and an illumination source. In particular, the systems and processes related to standardizing quantitative, microscopic analysis of target samples, such as biological samples. Exemplary biological samples include a cell, a group of cells, a tissue section, an array of tissue sections (e.g., a micro tissue array) and combinations of one or more of any of these. Biological samples can be treated with one or more stains. In some instances, the stains are immunohistochemical stains. In some instances, the immunohistochemical stains are fluorescent stains.

Generally, a microscope system includes an illumination source configured to illuminate a target sample, optics configured to produce a magnified image of the illuminated target sample, and a detector, such as a digital camera, configured to capture a digital image of the magnified image. Quantitative results can be obtained through manipulation of the captured digital images. Such image manipulation can include image processing techniques known to those skilled in the art. In at least some embodiments, one or more of such image capture and image manipulation is accomplished with the aid of a processor. The processor can include a computer implementing pre-programmed instructions.

The system also includes a calibration device configured to redirect a standardized sample of the illumination source to the detector. In at least some embodiments a system processor is configured to determine a correction factor for a given microscope. The correction factor can be determined from a measurement of the standardized sample of the illumination source obtained using the calibration device. The correction factor can be used (e.g., by the processor) to correct for any variations in intensity of a detected image of the target sample. In some embodiments, a system processor is configured with instructions (e.g., software) for obtaining the calibration factor. Alternatively or in addition, the system processor is configured with instructions for using the correction factor to correct detected images. Such calibration is useful to remove from any quantitative results, variability in intensity of the illumination source within the same microscope system, as may occur over time, and between quantitative results obtained using different microscope systems and/or different illumination sources.

In some embodiments, the calibration device includes a scattering surface positionable along an optical path between the illumination source and the detector so as to direct a scattered portion of light from the illumination source toward the detector. Variability in the detected scattered illumination can be used to develop such a correction factor.

In other embodiments a system processor is configured to determine or access a correction factor for the optical component of a given microscope. The correction factor can be determined from a measurement of the standardized sample using the optical component of the microscope. The correction factor can be used (e.g., by the processor) to correct for any variations in optical features of a given microscope impacting the intensity of a detected image of the target sample.

Microscope System

Systems and processes described herein are general applicable to any microscopy system incorporating an illumination source. Examples of at least some microscope systems in which the systems and processes can be used included optical microscopy, fluorescent microscopy, and confocal laser scanning microscopy. An exemplary microscopy system is the PM-2000™ instrument commercially available from HistoRx, Inc., of New Haven, Conn. The systems and processes are particularly useful for systems geared towards providing a semi-quantitative or quantitative result. Exemplary applications include the use of immunohistochemistry (IHC) as used within the field of pathology (See, for example, Immunohistochemistry and Quantitative Analysis of Protein Expression, by M. Cregger et al., Arch. Pathol. Lab. Med., Vol. 130, July 2006 at pgs. 1026-1030). Typically, these results are based on the intensity of staining of a sample examined using the microscopy system. Samples can be biological specimens. Stains can be general histological stains, special stains, IHC, FISH, chromogenic, fluorescent, etc.

According to Cregger et al., a diagnostic pathologist typically interprets IHC according to a subjective approach by using a binary positive-negative end point or a 3- to 4-point scale. With the assistance of a computer, an automated analysis can be obtained for target samples using a computer program to help eliminate the inherent variability of pathologist-based scoring. In immuno-fluorescence, a fluorescent product is deposited at the site of an antigen, allowing for visual localization of the antigen in the sample. After photographic capture, the reaction product may be quantified by image-analysis software. Furthermore the antigen may be located in a specific cellular (e.g., nuclear, organellular, cytoplasmic, membranous) or extra-cellular location (See, for example Camp et al, Nature Medicine 8(11) 1323-1327, 2002) Numerous computer-based programs have been designed for analysis of IHC, such as BLISS and IHCscore available from Bacus Laboratories, Inc. of Lombard, Ill., ACIS of Clarient, Inc of San Juan Capistrano, Calif., and AQUA® analysis of HistoRx, Inc. of New Haven, Conn.

Generally, for fluorescent IHC, multiple digital images (e.g., TIFF, JPEG, GIF, PNG) are obtained from the same target tissue sample stained with protein biomarker-specific antibodies and secondary fluorescent detection reagents. When optimized, the fluorescent stains provide a broader dynamic range than available by absorbance-based chromogenic stains. Each of the digital images can be obtained using a different optical filter configured to pass a respective one of the secondary fluorescent signals. Thus, at least one respective digital image is obtained for each of the secondary fluorescent signals. For quantitative analysis, the captured digital images are manipulated (e.g., using image processing software) to obtain a respective score of the tissue sample.

More specifically, the systems and processes are described in reference to an exemplary system illustrated in FIG. 1.

Referring to FIG. 1, an exemplary reflected-light fluorescent microscope system 100 includes a an excitation source 102, an objective lens 104, a sample supporting stage 106, a filter block 108', and an observation head 110. The sample supporting stage 106 is configured to support a sample under test along an optical axis and within a focal plane of the objective lens 104. The filter block 108' is also located along the optical axis between the objective lens 104 and the observation head 110. The filter block 108' is a three port device with two opposite ports disposed along the optical axis and a third port disposed off-axis. As illustrated, the third port can be orthogonal to a line joining the two opposite ports.

Illumination from the excitation source 102 is directed toward the orthogonal port of the filter block 108'. The filter block 108' redirects a portion of the illumination from the excitation source 102 toward the objective lens 104. The objective lens 104 preferably includes a relatively high numerical aperture thereby allowing it to capture a substantial portion of excitation light. The objective lens 104 functions as a condenser directing excitation light toward a sample under test placed upon the stage. In some embodiments, multiple objective lenses 104 (e.g., 4×, 10×, 20×, 40×, 60×) are included within a single nosepiece (not shown). The nosepiece can be manipulated to selectively bring different ones of the multiple objective lenses 104 into alignment with the optical axis to adjust magnification of the sample under test.

Illumination (emission) from the sample under test travels along the optical path through the objective lens 104 and into a first one of the opposite ports of the filter block 108'. At least a portion of the sample illumination continues along the optical path, exiting a second one of the opposite ports of the filter block 108' towards the observation head 110. As described in more detail below, the filter block 108' selectively filters illumination passed therethrough. In fluorescence microscopy, filtration can be used to selectively view emissions from different fluorophores (e.g., red, green, blue). As illustrated, the microscope system 100 can include multiple filter blocks 108', 108'', 108''' (generally 108), each filter block 108 being tuned to pass a selected emission wavelength toward the observation head 110. The different filter blocks 108 can be stored within a carousel or turret 115, allowing for rapid selection of a different filter block 108 without disturbing the sample under test. In some embodiments, the different filter blocks 108 are radially disposed within the turret 115 about an axis of rotation. The turret 115 is positioned with its axis of rotation parallel and to a side of the optical axis, such that one of the filter blocks 108' is aligned with the optical axis. Rotation of the turret 115 selectively moves one filter block 108' out of alignment and brings another one of the filter blocks 108'', 108''' into alignment with the optical axis.

The observation head 110 directs at least a portion of light from the filter block 108 toward an image collection device, such as a charge coupled device (CCD) camera 112. In some embodiments, the observation head 110 additionally includes one or more eyepieces (not shown) allowing for manual observation of the sample under test. Such an eyepiece can be used to adjust placement of a sample 107 upon the stage 106 and to coordinate positioning of the stage 106 before and during test. In some embodiments, a first shutter 117 is provided to control exposure time of the sample 107 to the excitation source 102. A second shutter 114 is provided to control exposure time of an imaging device, such as the CCD camera 112. As shown, the shutter 114 can be an independent component located along the optical path between the sample under test and the observation head 110. Alternatively or in addition to an independent shutter 114, the shutter can be integrated into the CCD camera 112.

The microscope system 100 also includes a controller 116. The controller 116 can be used for controlling the overall image acquisition process. Preferably, the controller 116 is in communication with one or more sub elements of the microscope system 110 to allow automated control of the system 100. In the exemplary embodiment, the controller 116 is in communication with one or more of the excitation source 102, an axial translator 119 (focus adjust) of the objective lens 104, the CCD camera 112, the shutter 114, the turret 115, and a stage positional controller 118. The controller 116 can include at least one microprocessor or computer 116 operating under the control of program code.

In operation, the controller 116 may send a signal to the stage positional controller 118 to position the stage 106, such that a selected region or spot 109 of the sample under test is brought into alignment with the optical axis. The controller 116 may also send a signal to the axial translator 119 configured to position and reposition the objective lens 104 along the optical axis with respect to the stage 106. For embodiments including a motorized nosepiece, the controller 116 may send a second signal to the nosepiece causing it to rotate a selected one of multiple objective lenses 104 into alignment with the optical axis prior to focusing. The controller 116 may also send a signal to the turret 115 causing a controlled rotation of the turret to select one of the multiple filter blocks 118. In response, the turret 118 rotates, bringing the selected one of the filter blocks 118 into alignment with the optical axis. The controller 116 next sends a signal to the excitation source 102 turning the source 102 on, at least momentarily, to illuminate the sample under test. The shutter 114 is normally closed blocking the optical path between the sample under test and the CCD camera 112. For some microscopes the light source 102 is turned on during initialization of the instrument. With fluorescent microscopes, the high-intensity lamps require a warm-up period to allow intensity of the source 102 to stabilize before any test samples are measured.

For such fluorescent systems, the light source 102 may remain on during operation. In such applications, a first shutter 117 provided between light source 102 and test sample is used to block illumination of the sample until ready to view the sample and acquire an image of the sample. Such limited exposure of the test sample to illumination may avoid bleaching of the sample. Optionally, a second shutter 114 is provided within the CCD camera 112. Upon receiving a trigger signal from the controller 116, the first shutter 117 opens for a predetermined exposure period before closing again. A second trigger signal from the controller is sent to the second shutter 114 associated with the CCD camera 112. This signal controls exposure allows a controlled sample of emission from the sample under test to reach the CCD camera 112. Thus, the first shutter 117 is open for at least the entire duration of an exposure controlled by the second shutter 114. In some embodiments, operation of the two shutters 114, 117 can be controlled by a common signal, or otherwise configured to operate in synchronization. Under control of the controller 116, the CCD camera 112 captures an electronic image of illumination from the sample under test. The image can be forwarded to the controller 116 or to an external system for analysis.

With optional independent control of the two shutters 114, 117, timing of each shutter can be varied to produce different effects. For example, in some embodiments, the first shutter 117 is opened to expose test sample for a predetermined period of time and then closed. This can be performed to expose a luminescent test sample to illumination from the source 102. The second shutter 114 could be operated after closure of the first shutter 117 to sample luminescence of the sample, without interference from source illumination.

In one particular embodiment, the a fluorescent microscope system is part of an integrated quantitative IHC analysis system, such as the AQUA® analysis PM-2000™ system, commercially available from HistoRx, Inc. of New Haven, Conn. AQUA is a registered trademark of HistoRx, Inc. The IHC analysis system consists of the following components assembled in a light-tight enclosure: a fluorescent microscope, such as the Olympus BX51 epi-fluorescence microscope, commercially available from Olympus America, Inc. of Center Valley, Pa.; the microscope is equipped with a motorized nosepiece to control selection among different objective lenses (e.g., 4×, 10×, 20×, 40×, 60×), and a motorized filter turret to control selection among different filter cube selection (e.g., in DAPI, Cy2, Cy3, Cy5 and Cy7 or equivalent wavelengths). The system also includes a motorized stage, such as the Prior Scientific part no. H101A. The PCI card that drives the stage is Prior Scientific part no. H252 motorized stage commercially available from Prior Scientific, Inc. of Rockland, Mass. The control card occupies a PCE expansion slot within a computer controller. Focus control is facilitated by integrated software. The system also includes a light source, such as the X-CITE 120 system, commercially available from EXFO Life Sciences & Industrial Division of Ontario, Canada, which is equipped with a mercury/metal halide lamp; a monochromatic digital camera for images capture, such as the QUANTIFIRE camera, commercially available from OPTRONICS of Goleta, Calif.; and a computer controller. In the exemplary embodiment, the computer is a personal computer running WINDOWS XP or higher operating system environment.

Instrument Standardization

In order to standardize quantitative results obtained using a particular system, a system intrinsic factor can be determined to account for intensity variability of the excitation source and device variability i.e., along the optical path. In order to achieve this, a measurement of the intensity of the excitation light source may also be obtained for example by using an inline lamp intensity measuring tool. Also a measurement of a standard or a calibration sample i.e., a calibration microscope slide may be obtained using the particular system to define one or more optical path factors. Use of such a calibration slide is particularly useful for fluorescence-based IHC applications, in which sample fluorescent regions of the calibration slide emit radiation within respective bandwidths. The fluoresced emissions allow for characterization of an optical path at each of the one or more respective wavelengths. These measurement can be obtained simultaneously or separately.

Light Source Intensity Measurement

Generally, a process or instrument to provide for direct measurement of the light source intensity is most conveniently incorporated into the system. A light source sampling instrument provides for capturing a sample of the light source intensity. In some embodiments, a sampled portion of the light source intensity is directed to a detector (e.g., a camera). The light source intensity measurement can be accomplished independent of the optical portion of the system.

More generally, the sampling process or instrument accesses a sample of the light source at intensity levels below a light source detector saturation threshold and above a noise level. For example, the light source intensity can be sampled by an electronic sensor within an exposure period (e.g., 10 milliseconds). Alternatively or in addition, the light source can be attenuated to ensure that the obtained sample falls within the sensitivity range of a given detection device.

The sampled light source intensity can be accomplished using an in line radiometer, resulting in a measurable voltage representative of the light source intensity. Such measured voltages can be processed automatically by the system. For example, the voltages can be sent to a processor for further processing. In some embodiments, the voltage levels are converted into a digital representation of the voltages. Such conversion can be accomplished using analog-to-digital conversion, allowing for digital processing of the sampled voltage. The digital processing can be accomplished by one or more of software running on the processor and hardware adapted for digital signal processing.

The sampled light source intensity can be obtained directly or indirectly from the light source. In some embodiments, the sampled light source intensity is obtained independent of at least some other parts of the system, such as the optics (e.g., an objective lens), that may independently impact the sampled result. Alternatively or in addition, the sampled light source intensity is measured at light source itself, thereby avoiding any effects of the microscope.

Calibration Cube

In some embodiments, a special calibration instrument can be used for the purpose of obtaining a sample of the light in order to measure the intensity of a light source. Preferably, the calibration instrument allows a relative light intensity measurement to be obtained substantially simultaneously with the target sample image. In at least some embodiments, this is accomplished by switching a special calibration instrument into the optical path to obtain the relative light intensity measurement, and then out of the optical path to obtain the sample image. For example, if the microscopy system is a fluorescent system using multiple filter cubes pre-loaded in a rotatable turret 115, the calibration instrument can be included as one of the filter cubes (i.e., a calibration cube) within the turret 115. This will allow for the calibration cube to be interchanged with the other filter cubes automatically during the course of measurements.

Generally a filter cube has openings on the top, bottom, and front faces of a cube-shaped frame. The front opening or port allows light from the illumination source to enter the cube, after which the light is reflected off an internal reflective surface generally positioned at 45 degrees to the axis of the entering light. The angled reflective surface (e.g., mirror) redirects a reflected portion of sampled light toward the bottom opening or port of the cube. In operation the redirected light may be used to illuminate a target (a tissue sample, etc.). The redirected light travels along an optical path that may include objective optics as provided in microscope systems. At least some portion of the illuminating light may be reflected from the sample. For at least some applications, stimulated light may also be emitted from the sample, as through fluorescence. In either instance, at last a portion of light from the sample (reflected and/or emitted) travels back along the same optical path, entering the cube from the bottom port. At least a portion of the light entering the calibration cube travels through the angled reflective surface of the angled mirror along the optical path and exits through the top opening or port of the cube and to an imaging device.

In some embodiments, the calibration cube is a modified filter cube in which a light scattering surface is affixed to block the bottom opening. In operation, light entering the cube is reflected off the internal angled reflective surface and directed toward the light scattering surface. The reflected light illuminates the light scattering surface. At least a portion of scattered light from the light scattering surface is directed back up through the internal reflective surface, exiting at the top opening of the cube toward the imaging device. The same calibration cube having the same light scattering surface can be used to sample light from the same illumination source at different times and/or different illumination sources. In this manner the calibration cube provides a means for sampling light intensity scattered off of a standardized surface (instead of the typical sample) to be captured by the imaging device, and usable to determine a standardized light intensity measurement. Beneficially, such sampling can be accomplished without repositioning one or more of the target slide and the objective lens.

The calibration cube serves as an in-line access tool for measuring intensity of the lamp. In cooperation with a processor 116 (FIG. 1), the intensity measuring tool not only allows for tracking lamp intensity deviations, but also enables a straightforward means of normalizing quantitative results. Accounting for such lamp intensity deviations promotes precision measurements of biomarker expression in a tissue sample. For example, data from captured images obtained by several microscopy systems equipped with identically constructed, standardized, calibration cubes, can be corrected to effectively eliminate any contributions that would otherwise have been attributable to lamp intensity variations. Thus, quantitative analysis results, such as AQUA scores obtained from corrected images may be compared for a reliable indication of target sample differences, not system differences. Light source calibration data obtained using the calibration cube can be collected, stored and accessed from various system software applications, such as system initialization and setup programs, image acquisition programs allowing for minimal user interaction and negligible time and cost.

Figure 2:
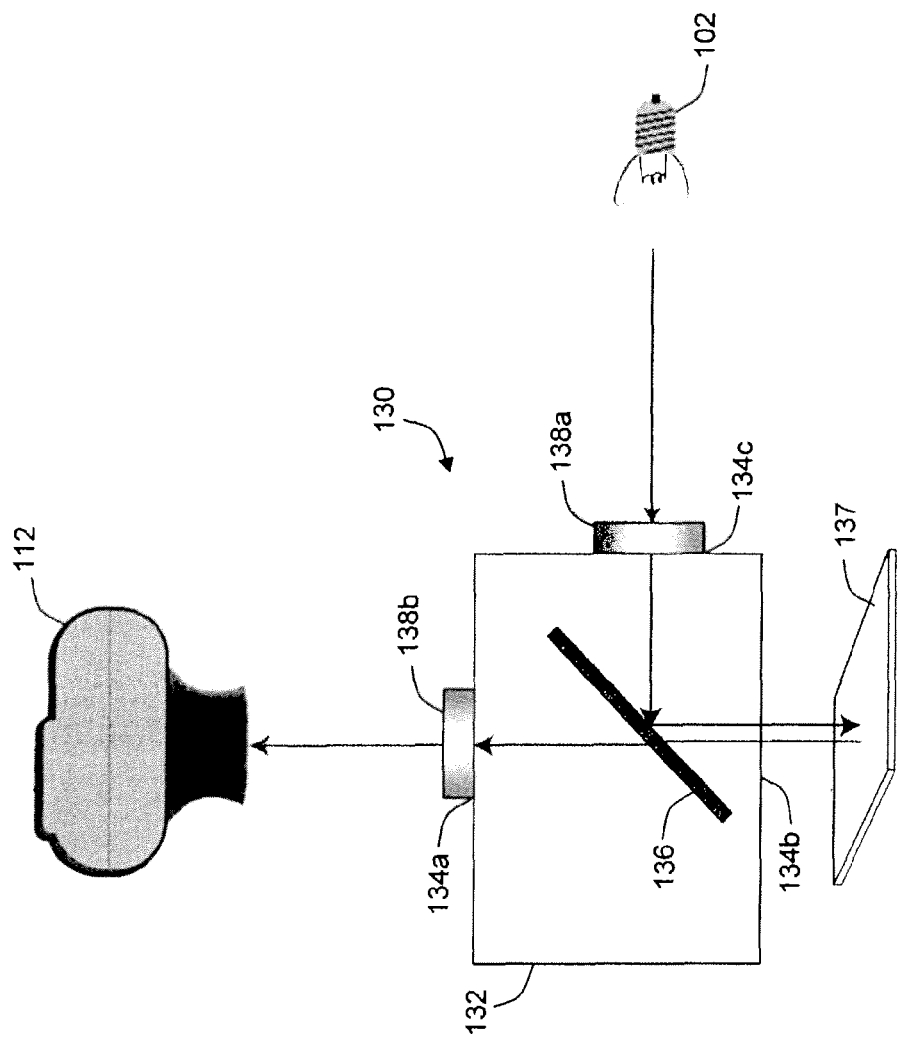
FIG. 2 shows a schematic diagram of a calibration instrument constructed in accordance with principles of the present invention.

In one embodiment, referring to FIG. 2, a calibration instrument, or cube 130 includes a housing 132 including a first port 134a and a second port 134b opposite the first and aligned therewith along a common optical axis. The housing 132 also includes a side port 134c that is not aligned with the optical axis. As illustrated, the side port 134c is orthogonal to the optical path. The housing 132 also includes an internal reflective surface 136 forming a nonzero angle $\theta$ with the optical axis. Illumination is received from an excitation source 102 through the side port 134c. The reflective surface 136 is angled to redirect a portion of the received excitation light along the optical axis, through the second port 134b. The calibration cube 130 also includes a light scattering surface 137 positioned relative to the second port 134b to scatter, or return excitation light in an opposite direction along the same optical axis. At least a portion of the scattered excitation light passes through the reflective surface and exits the housing 132 through the first port 134a. This scattered light can be detected by a CCD camera 112 aligned with the first port 134a.

In alternative embodiments, a calibration instrument can be formed without a mirrored surface. For example, considering the same general structure of the cube 130 illustrated in FIG. 2, the internal reflective surface 136 can be replaced by a light scattering surface. The light scattering surface can be angled within the cube to promote redirection of scattered light from the illumination source 102 through the side port 134c.

Figure 3:
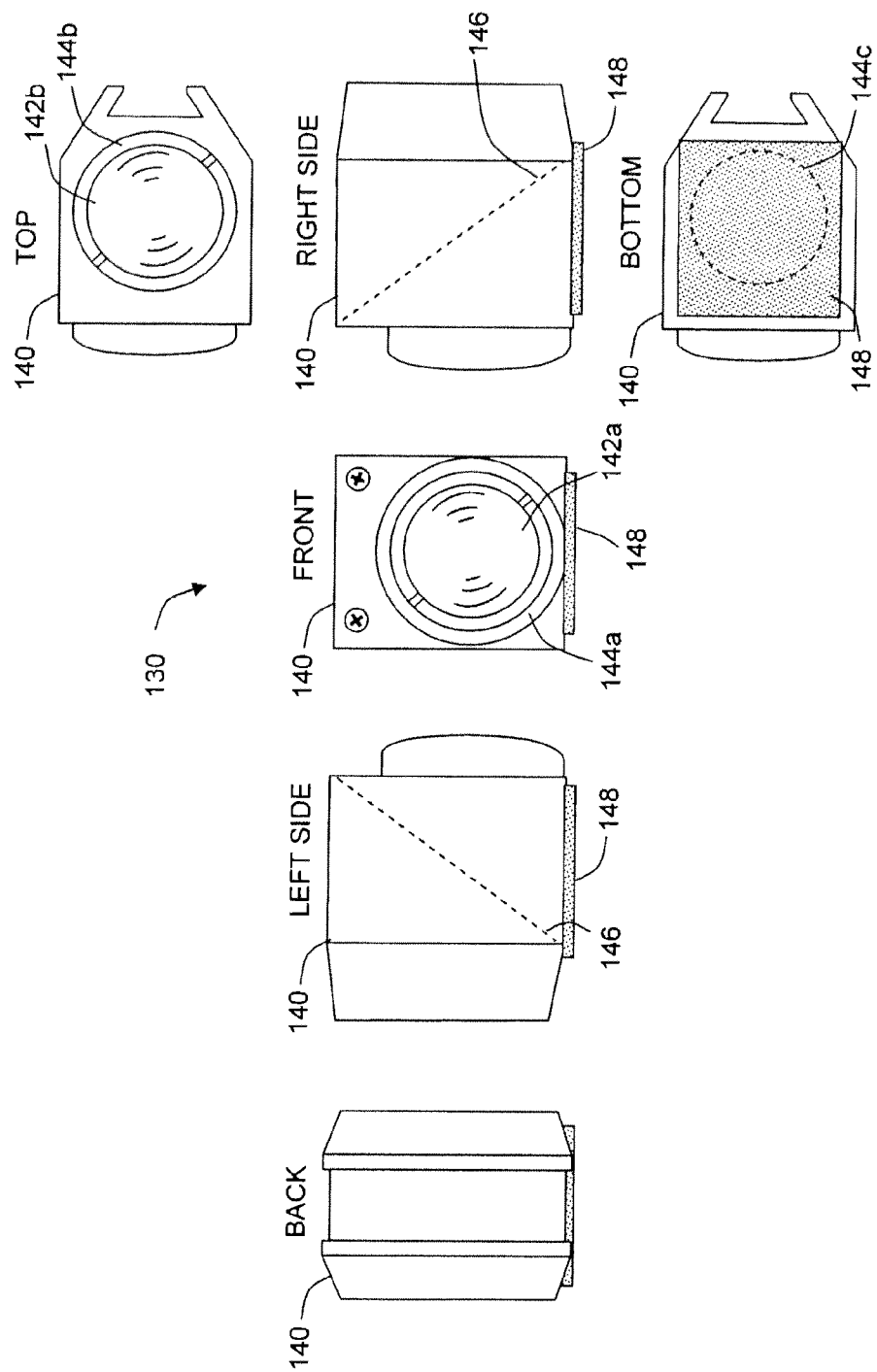
FIG. 3 shows front, back, left side, right side, top, and bottom views of an exemplary calibration instrument constructed in accordance with principles of the present invention.

The light scattering surface 137 is generally uniform, having a surface that is a minimally reflective surface (e.g., a matte surface) and provides uniform reflectance/fluorescence across the field of view which provides for also measuring a uniformity of sampled light from the light source. In at least some embodiments, the light scattering surface 137 scatters light substantially uniformly. Material forming the light scattering surface 137 should be able to withstand high temperatures and light intensity without degradation or variation. The material is preferably rigid or at least semi-rigid and not susceptible to yellowing, degradation, or photo bleaching. Furthermore the material should be reproducible, and relatively inexpensive. In some embodiments, certain metallic, ceramic or plastic materials meeting these conditions are acceptable. Ceramic materials, such as gold and white ceramic targets are commercially available from Avian Technologies, Inc. of Wilmington, Ohio. Such materials can be used for the calibration cube filter 148 (FIG. 3). Alternatively or in addition, such materials can also be used for standard calibration slides. In an alternative embodiment a piece of flat filter paper may be used.

In fluorescent microscope applications, emission light detected by the CCD camera 112 is substantially lower in intensity than the excitation light. In order to avoid saturation of the CCD camera 112 when detecting the excitation source itself, one or more filters are included between the excitation source and the camera 112 to attenuate the light to a sufficiently low level. In some embodiments, one or more neutral density, or gray filters are provided along an optical path between the excitation source 102 and the CCD camera 112. For example, a first neutral density filter 138*a* is provided at the side port 134*c* attenuating excitation light entering the housing 132. A second neutral density filter 138*b* is provided at the first port 134*a* attenuating scattered light returned to the CCD camera 112. The attenuation values of each filter 138*a*, 138*b* can be the same or different, as long as their combined effect ensures that the CCD camera 112 will not be saturated by scattered light from the excitation source 102.

Figure 4:
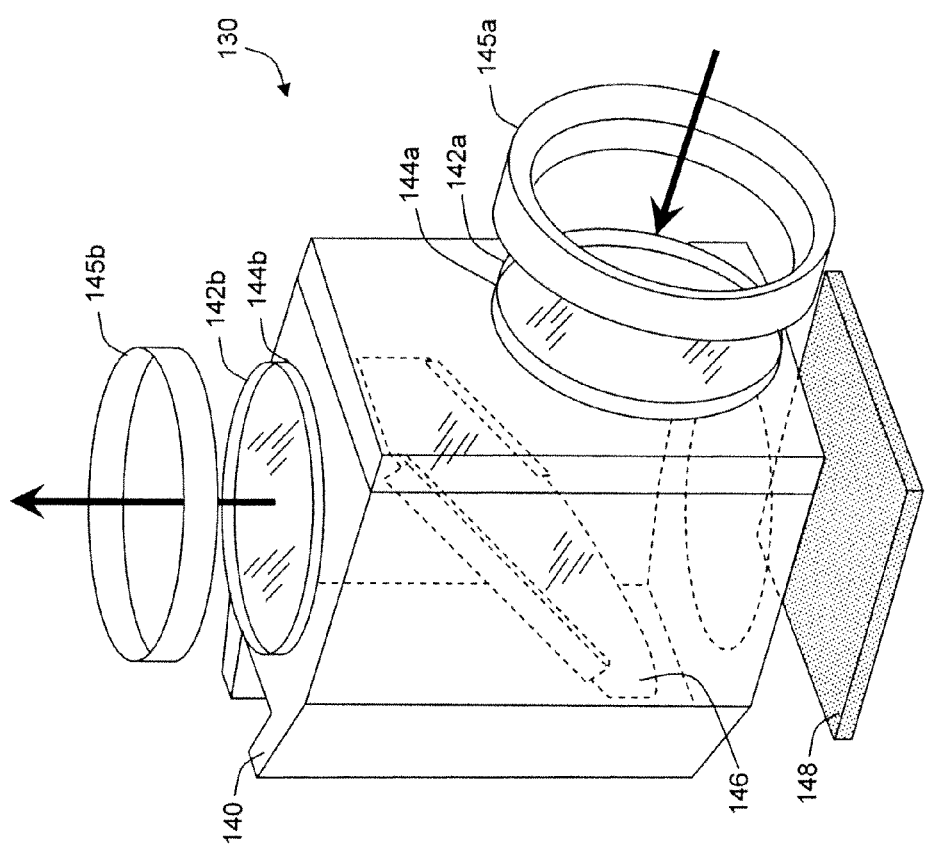
FIG. 4 shows an exploded top perspective view of the calibration instrument of FIG. 3.

EXAMPLE: In an exemplary embodiment of the calibration cube 130 shown in FIG. 3, the cube 130 consists of a regular OLYMPUS filter housing or holder 140 (OLYMPUS Part no. U-M610, U-MF2 BX filter holder cube) equipped with neutral density filters 142*a*, 142*b* at the emission and excitation openings 144*a*, 144*b* and a 50/50 dichroic mirror 146. In some embodiments, the filters 142*a*, 142*b* are retained in proximity to the openings 144*a*, 144*b* using respective filter frames 145*a*, 145*b* (FIG. 4).

The bottom of the housing 140 has a light scattering surface 137 (FIG. 2); 148 (FIGS. 3, 4) mounted over the port 144*c* (FIG. 3) positioned to completely block the sample opening 144*c*. A top perspective exploded view of the exemplary calibration cube is shown in FIG. 4.

EXAMPLE: In an exemplary embodiment, the calibration cube 130 includes two neutral density filters, 25 mm, such as Chroma cat. no. 2200a, commercially available from Chroma Technology Corp. of Rockingham, Vt. The cube 130 also includes a dichroic mirror, 50/50 beam splitter, such as Chroma cat. no. 21000, housed within a filter holder (cube) 140, such as Chroma cat. no. 91018. The scattering surface can include filter paper 148, such as VWR cat #28306-153, commercially available from VWR of West Chester, Pa. Which particular brand of filter paper used is not important, but preferably the same filter is used among all calibration cubes 130 of different microscope systems to ensure uniformity of results. As will be described below, even this is not critical, as relative measurements can be made for calibration cubes 130 using different filter paper 148 compared to a common, or standardized calibration cube. Such a comparison can be used to determine an offset to be accounted for in the correction process.

In other embodiments, the calibration cube 130 includes a microscope filter holder, such as OLYMPUS Part no. U-M610, U-MF2 BX filter holder cube, commercially available from Chroma Technology Corp of Rockingham, Vt., cat #91018. Other commercially available filter cubes compatible with the microscope system may be used. In a particular example, the neutral density filters are ND 1.0 Part no. UVND1.0, ND 1.0 neutral density filter, 10% transmittance, 25 mm, and ND 2.0 Part no. UVND2.0, ND 2.0 neutral density filter, 1% transmittance, 25 mm, commercially available from Chroma Technology Corp. The 50/50 beam splitter/dichroic is Chroma Part no. 21000, 50/50 beam splitter, 38×26 mm. WHATMAN Filter Paper, Grade 1, Cat No. 1001-125, VWR of West Chester, Pa. is affixed to the bottom of the cube. Beneficially, the filter material scatters an appropriate amount of light back towards the CCD camera 112, such that an image can be acquired by the camera 112 in a reasonable exposure period. For example, the exposure period can be chosen between approximately 3 and 200 milliseconds. Other exposure periods can be selected outside of this range, provided they are appropriate for the applicable camera capabilities.

Scattered light received at the CCD camera 112 is preferably below the level of camera saturation for the exposure time selected with consideration given to variations in other cube assemblies which may be brighter or dimmer. Less desirable, but acceptable, is a scattering material that provides usable signal (below the limit of camera saturation) for exposure periods greater than about 200 milliseconds.

For use in standardization of systems, the specially designed calibration filter cube 130 can be installed within the turret of the microscope system 100 (FIG. 1). This calibration cube 130 serves as an inline lamp intensity measuring tool that provides a means for measuring excitation light intensity, by sampling scattered light that is directly proportional to the incident excitation light source intensity. Thus, the sampled scattered light can be used to track variation in light intensity of the excitation source during use. Such variations in intensity might occur from long-term effects of the excitation source such as aging, in which intensity of the source may be diminished slowly during the normal process of aging. Variations may also result from short term effects that may result from other effects, such as ambient temperature variations, device temperature variations from device heating, and excitation voltage and current among others.

During image acquisition in which a sample of the illumination source light intensity is obtained, the light traveling through the excitation neutral density filter 142*a* is attenuated, passed through the beam splitter 146 and reflected off of the calibration material 148 (i.e., white paper target). Reflected (or scattered) light is then further attenuated at the emission neutral density filter 142*b* and then captured by the camera 112 (FIG. 4). The neutral density filters 142*a*, 142*b* are arranged such that the excitation light is highly attenuated to reduce the intensity impinging on the calibration material 148. The emission filter 142*a* allows more light through and thus helps reduce intensity observed by the digital camera 112.

Calibration Cube Standardization (CC)

Individual calibration cubes may have intrinsic variations due to material differences that are preferably accounted for in order to normalize quantitative results obtained across instruments. In manufacturing a universal standard cube may be identified. Thereafter all manufactured cubes are compared to the universal standard cube by sampling of a consistent light source with each new cube and any inherent differences are accounted for, i.e., by applying a cube correction or cube calibration factor (CC). The cube calibration factor is preferably determined initially for every new calibration cube. In some instances, the cube calibration factor can be determined periodically thereafter for system maintenance, and when material properties of a cube may have changed (i.e., due to aging).

EXAMPLE: In order to characterize a number of similar calibration cubes, results were obtained for each of a batch of five cubes (J1-J5) using the same excitation source and camera configuration. A specific one of the cubes (i.e., J5) was designated as a reference cube for a group. This cube could be referred to as a universal standard cube. The reference cube J5, along with the other cubes to be tested, were installed simultaneously into the turret 115 of the microscope system 100 (FIG. 1). Images of the sampled illumination from the illumination source obtained through the calibration cube 130 were acquired by the digital camera 112 for each cube J1-J5. Light intensity measurements so obtained were compared between the different calibration cubes being tested. A ratio of intensity measured for each test cube J1-J4 to the intensity measured using the reference cube J5 was determined representing a cube calibration factor (CC). In an exemplary experiment, sixteen measurements were collected for each of the different cubes J1-J5. A ratio of the intensity obtained for each cube J1-J5 to intensity of the reference cube J5 was determined. Table 1 shows the CC values determined for the five cubes as compared to the reference cube (J5). Since the construction of the cubes J1-J5 was similar, the ratios of the intensities are all close to 1.

TABLE 1

| Cube Calibration Factor (CC Values) | |
|---|---|
| Calibration Cube No. | CC |
| CC2 | 0.894 |
| J1 | 0.929 |
| J2 | 0.989 |
| J3 | 0.907 |
| J4 | 0.883 |
| J5 (reference cube) | 1.000 |

Figure 5:
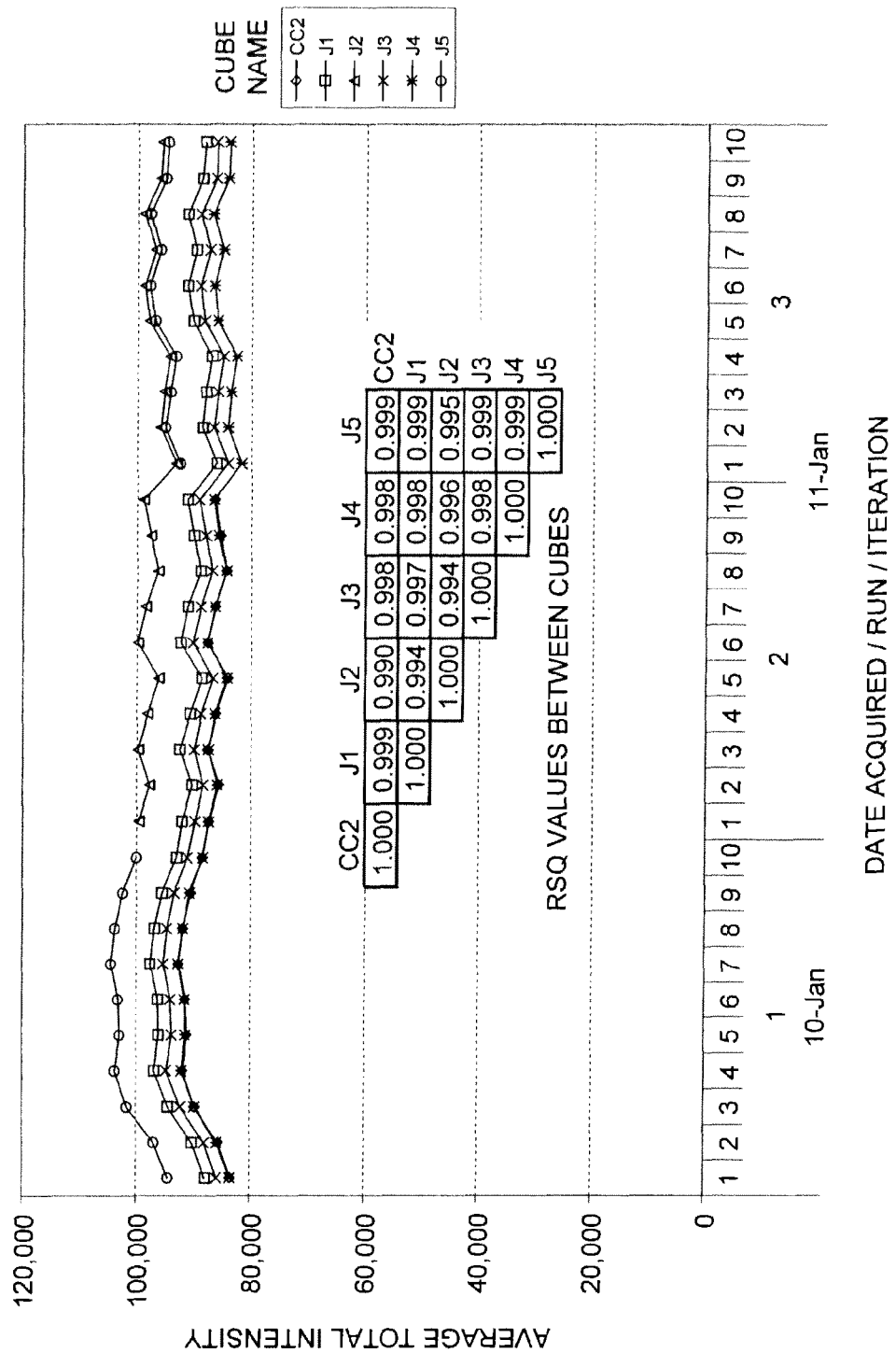
FIG. 5 shows temporal variation of excitation lamp intensity obtained for different calibration instruments in accordance with principles of the present invention.

To determine temporal effects, light intensity measurements were measured for each cube using the same instrument over a two-day period. A minimum of ten measurements were taken through each cube on each day (sum of pixel intensities in the captured image). The results are shown graphically in FIG. 5 as an average total intensity on a scale of 0 to 120,000. The results show that light source intensity fluctuations were recognized in the measurements using all cubes J1-J5. Preferably, correlation coefficient $R^2$ values between all cubes are relatively high (e.g., >0.95). The test results suggest that during actual specimen image acquisition, the intensity of the light source can fluctuate. These fluctuations can occur over a short duration each time the lamp is ignited and as slow variations occurring over time while a lamp remains ignited.

Light Source Standardization (LS)

In an exemplary procedure for determining a light source standardization LS, pixel intensities of a captured image of the illuminated calibration surface are combined in a sum. Different ranges can be identified depending upon the particular intensity scale values used for the pixels, as well as the number of pixels in the image. Exemplary LS values obtained using the AQUA® system range from about of 20,000 to 120,000. A ratio can be formed from the LS factor and a chosen intensity value. Such a ratio can then be used to compensate target sample data to essentially remove light source variation. In an exemplary embodiment, a ratio is formed using a chosen value of 100,000 and an LS factor falling within the AQUA® system range.

Device Optical Path (OP) Measurement

Generally an optical path correction procedure uses a calibration sample (e.g., a calibration slide) providing a known reflectivity and/or fluorescence that is usable in direct measurement of the specific device or system's optical path performance. A calibration sample can be used to obtain a correction factor for the intrinsic optical path performance of a given microscopy system. When different microscopy systems are similarly corrected, target sample results obtained from the different systems may be compared reliably across the different microscopy systems.

Most generally the calibration sample has the following characteristics:
- displays some characteristics of the samples typically analyzed on the system (i.e., for fluorescent systems, these characteristics can include wavelength of excitement/emission);
- constructed using a uniform material, with optical properties (e.g., reflectivity) that are reproducible, available, and inexpensive;
- for at least the fluorescent applications, the uniform material can be opaque (i.e., a ceramic, etc);
- for bright field transparent applications, the uniform material attenuates light source, if necessary, to an acceptable level for the detector; and
- provides minimal bleaching (for fluorescent systems).

Variations along an optical path of a given microscopy system will not likely vary to any significant degree over time for the same system. Thus, there is no apparent need to re-perform the optical path correction procedure during normal operations. In at least some embodiments, the optical path correction factor is determined at the time of manufacture. The optical path correction factor can be re-determined after servicing (e.g., cleaning) of the microscopy system.

Control or Calibration Slide

A standardized instrument calibration sample (control slide or calibration slide) is used for acquiring data in a particular system to be calibrated to approximate the light throughput efficiency of a specific microscope system and optical configuration. For example, the control slide can be a Fluorescent Reference Slide Set XF900, providing a blue or green fluorescent reference slide commercially available from Omega Optical Inc. of Brattleboro, Vt. Other uniform sample materials may be used so long as sufficient signal in each channel (i.e., wavelength) may be acquired within the set exposure time (e.g., between about 3 and 1000 milliseconds, or current range of the CCD camera 112) and the material preferably demonstrates minimal bleaching over a standard number of runs. The sample material should be reproducible such that it can be used for standardizing each instrument and sized to fit on the microscope stage. The material preferably emits or reflects a light signal with spectral components in the appropriate wavelength band(s) to be acquired through each filter cube in use on the microscope system, in an environment of low specular reflection. Other examples include, but are not limited to, alternative colored plastics, paper and ceramic reflective materials, metallic surface or surfaces coated with various inks and dyes.

EXAMPLE: A calibration slide was placed on the stage of a microscope system 100 previously fitted with a pre-standardized calibration cube 130 (FIG. 2) in the filter turret 115 (FIG. 1). Two different instrument control slides were tested: sample 1 having a spectra approximating FITC/GFP (green excitation) and sample 2 having a spectra approximating DAPI/Indo/Fura (Blue excitation). Calibration slide 1 was illuminated, and an image obtained of the fluorescence emission of the sample through each of three different filter cubes

Figure 6:
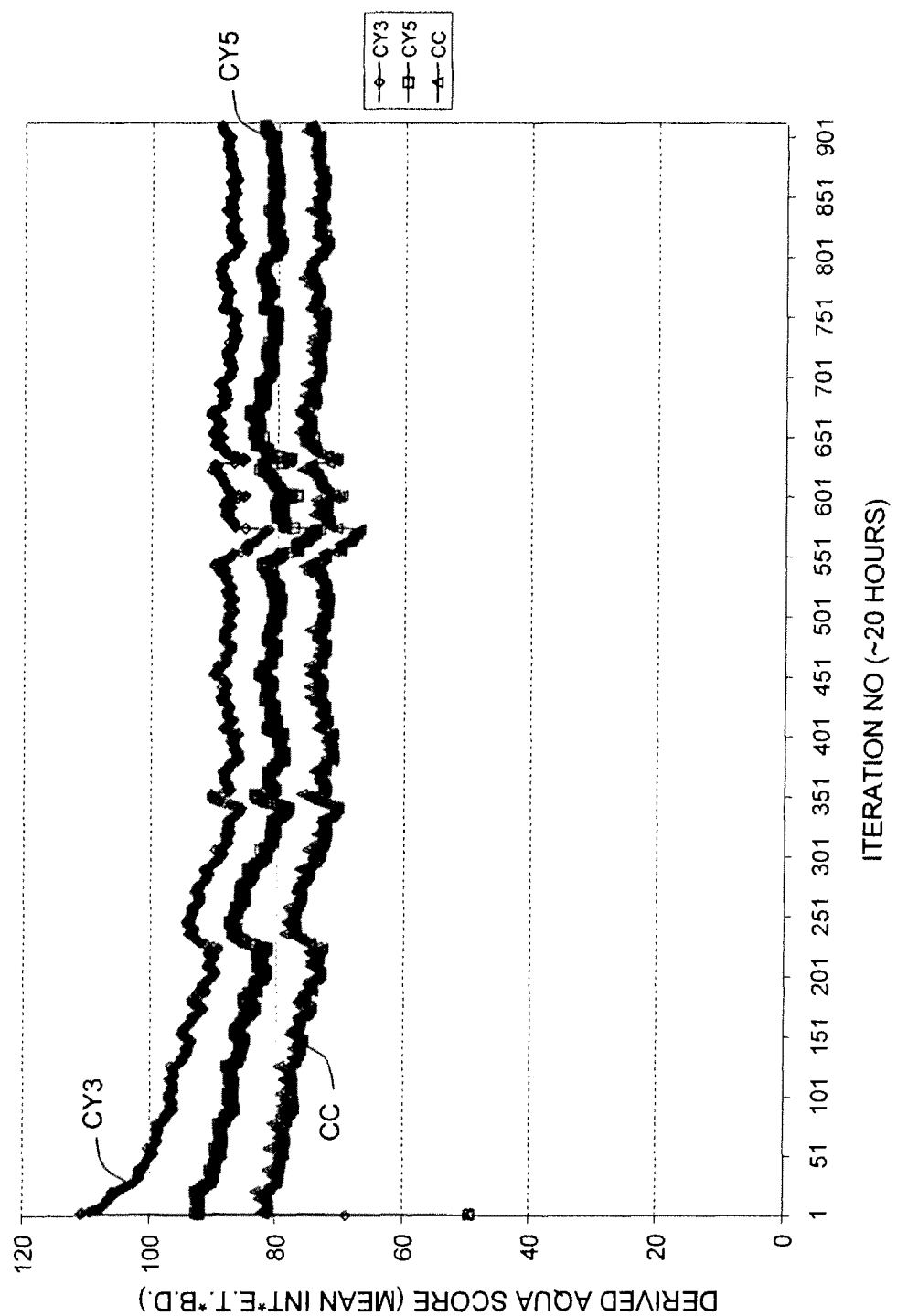
FIG. 6 shows temporal variation of qualitative results for multiple channels of a first calibration slide.

108 (FIG. 1), one for each channel and the calibration cube. Over 900 iterations were performed over a period of about thirty hours. Quantitative results, For each channel per iteration an intensity score ("derived AQUA® score") was calculated: mean intensity multiplied by exposure time multiplied by bit depth (i.e., 0-255) The light intensity through the FITC channel when using sample 1 was too bright indicating this material is not ideal for normalizing light fluctuations when acquiring in this channel, see results described for sample 2 below as an alternative. The results were graphed as the AQUA analysis score verses iteration for slide 1 (FIG. 6) for calibration slide intensity scores obtained in each Cy3, Cy5 channels and separately for the calibration cube. Essentially an identical light intensity pattern was obtained using instrument control sample 1 in the Cy3, Cy5 and calibration cube channel indicating the variability is unlikely due to bleaching of the instrument control slide material. Rather, variation is indicative of true light intensity variability inherent to the system 100. A subtle long-term decrease in quantitative measurements is observable over at least the first half of the samples. Superimposed on this are relative short-term variations in both directions. Interestingly, similar trends are observable in the measurements obtained for each of the different channels independently, suggesting that the variation is due at least in part to fluctuations in the intensity of the excitation source.

Figure 7:
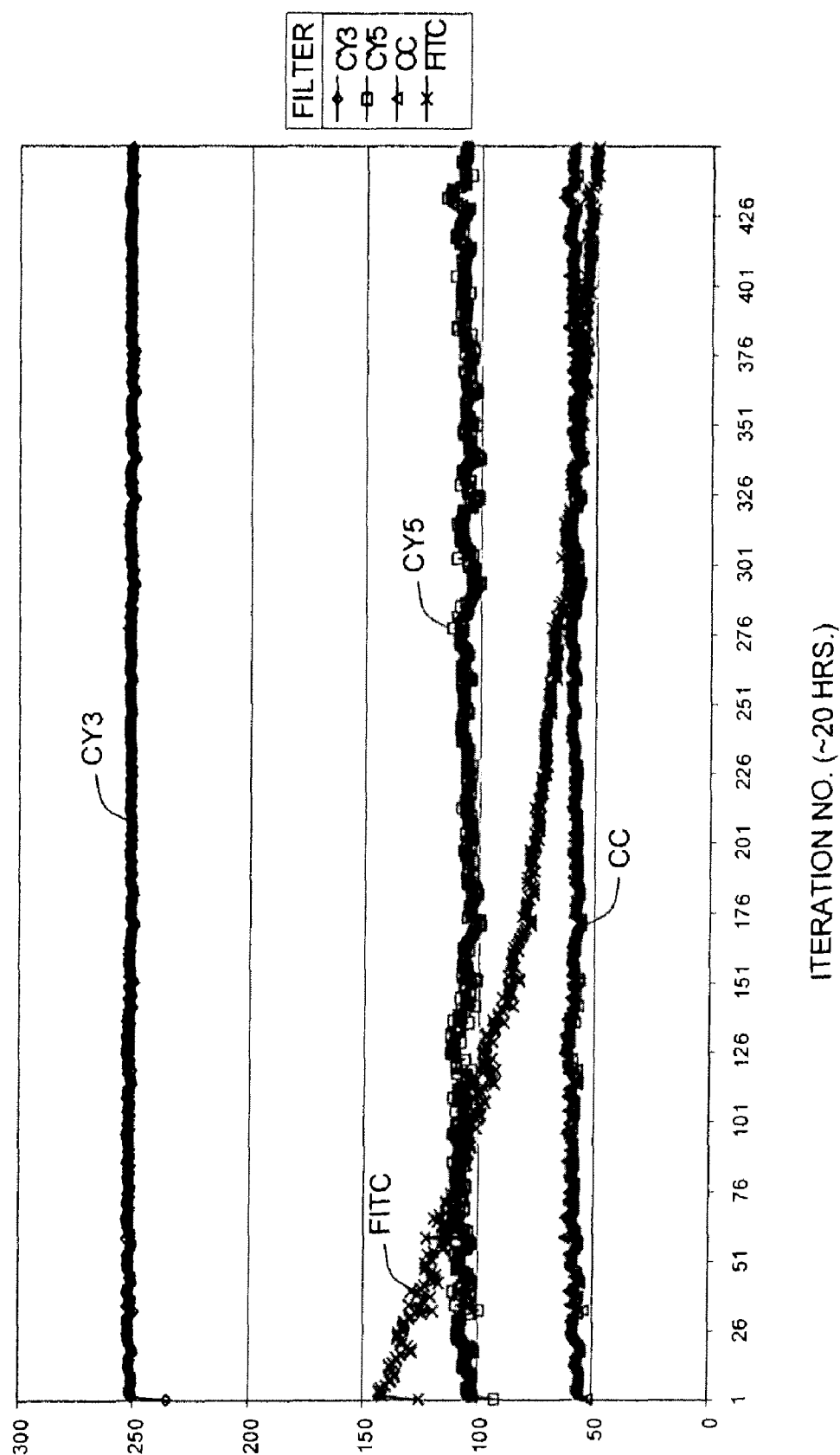
FIG. 7 shows temporal variation of qualitative results for multiple channels of a second sample slide.

Light source variability was further tracked by acquiring images of the second calibration slide (spectra approximating DAPI/Indo/Fura, blue excitation) through Cy3, Cy5, and FITC channels, and the calibration cube over approximately 20 hours for approximately 450 iterations. In an exemplary embodiment, quantitative results, such as the "derived AQUA scores" discussed above, were determined for each iteration. The results were graphed as the AQUA analysis score verses iteration for slide 2 (FIG. 7). Essentially an identical light intensity pattern resulted from using instrument control sample 2 in the Cy3, Cy5 and calibration cube channel indicating the variability is unlikely due to bleaching of the instrument control slide material. Rather, variation is indicative of true light intensity variability inherent to the system 100. The light fluctuation pattern seen through the FITC channel when using sample 2 was on scale and could be used for standardizing when images are to be acquired in this channel. Modest bleaching of the slide material is evident as a negative slope in the FITC channel over many iterations. Such bleaching is unlikely to adversely impact images acquired under normal operating conditions. Ideally the instrument control slide is replaced after about 10% bleaching has occurred. For example after 231 runs for sample 1 and approximately 20 runs with sample 2.

Instrument Optical Path Standardization (OP)

The measurement of signal at the digital camera 112 results from light that has traveled from the excitation source 102 (FIG. 1) through the microscope system 100 and has been modified by the intrinsic properties of that system 100 and the sample 107 being measured. The optical path of an instrument 100 may comprise the light pipe which travels from the excitation lamp to the microscope, the filter cubes 108 and associated optics for each fluorescent channel and the objective lens 104 being used. A machine intrinsic factor (OP) that corrects for variations along this optical path can be established for each device 100 in order to standardize results obtained across devices 100.

To calculate the machine intrinsic factor for a specific system, multiple images (e.g., 16 images) were acquired of a standard instrument control slide 107. For each system being standardized, the instrument control slide 107 was of the same material in the same configuration—presumably to yield the same results, but for effects of the system 100. Immediately after camera acquisition of a single field of view using a specified light filter cube 108 (e.g., FITC, Cy3 or Cy5 filter cubes), the filter turret 115 was turned so as to align the calibration cube 130 (FIG. 2). The calibration cube 130 was separately imaged, without disturbing either the objective lens or the sample (i.e., control slide 107) under test. Exposure times for each channel were fixed. A ratio of the calibration cube intensity to the observed signal intensity in each channel provided a machine intrinsic factor for the microscope system optical path efficiency for each filter. This value is applicable for that system in that specific configuration. The configuration is determined by such features as magnification, light filter, and optics.

The machine intrinsic factor of the system can also be scaled by referencing it to a specific value. The machine intrinsic factor was determined using data obtained using a non-bleached instrument control slide, at exposure times chosen to avoid saturation, from multiple runs (e.g., five runs) and in independent experiments on different days. The intrinsic value was calculated for each run. The % CV between run intrinsic values was extremely low such that one run was effective for calculating intrinsic values.

EXAMPLE: Table 2 shows the resulting machine intrinsic factors for five instruments across filters for three channels: FITC, Cy3 and Cy5.

TABLE 2

Machine Intrinsic Factors (OP Values)

| Instrument | FITC-OP | Cy3-OP | Cy5-OP |
| --- | --- | --- | --- |
| 1 | 1.15 | 1.14 | 1.09 |
| 2 | 1.61 | 1.49 | 1.86 |
| 3 | 1.46 | 1.38 | 1.18 |
| 4 | 1.00 | 1.00 | 1.00 |
| 5 | 1.38 | 1.07 | 1.32 |

Machine intrinsic factors were further scaled as the intrinsic value/empirical value, where the empirical value was the lowest average value recorded on the particular system. Intrinsic values were determined using two different blue instrument control slides and were found to be reproducible regardless of which slide was used. Average values and percent coefficient of variation (% CV) values were calculated. Preferably, the % CV is less than about 20%, more preferably the % CV is less than about 5%.

Standardization

The standardization factors described above (CC, LS, OP) were used to transform quantitative data collected on each individual microscope system to that of an idealized system. When applied to more than one system, data obtained therefrom are normalized, such that any influence of the respective microscope and light source fluctuations to the results were mitigated.

Figure 8:
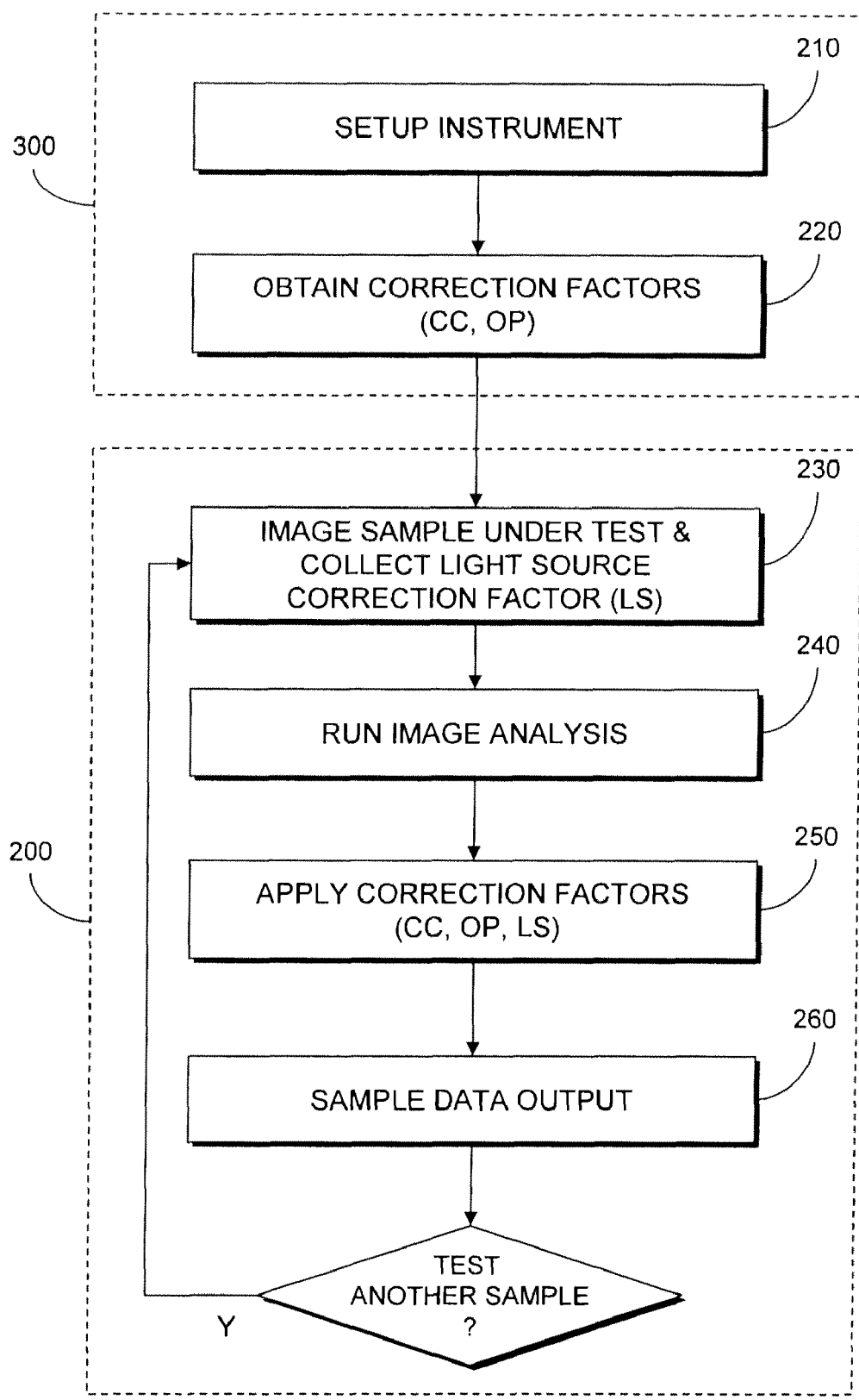
FIG. 8 shows a flow diagram of a process for standardizing qualitative analysis results in accordance with principles of the present invention.

Referring to FIG. 8, a flow diagram of a process for standardizing qualitative analysis results includes a preliminary initialization procedure 300 followed by a test sample procedure 200. As part of the initialization procedure 300, the instrument is setup at step 210. Instrument setup includes configuring the microscope system 100 (FIG. 1) with the appropriate excitation source 102, filter cubes 108 (FIG. 1) and calibration cube 130 (FIG. 2), ensuring that the controller 116 (FIG. 1) includes the proper program control, and performing any initialization routine that may be required for the microscope system 100 and CCD camera 112. Once instrument setup is complete, the CCD camera 112 is capable of obtaining images of a sample under test using the microscope system 100 under control of the controller 116. Once setup, a correction factor (CC) for the calibration cube 130 and a machine intrinsic factor (OP) for the microscope system 100 are obtained at step 220. As described above, the machine intrinsic factor (OP) may be determined at the time of manufacture, and/or at the time of servicing/repair of the microscopy system and stored for later use. Thus, obtaining the machine intrinsic factor OP may included looking up a pre-stored value. One or more of these factors (CC, OP) can be stored by the controller 116, or image analyzer for later use in analyzing images of test samples.

As part of the test procedure 200, a sample under test is imaged by the system 100 at step 230. A light source correction factor (LS) is obtained during this step. In more detail, an actual test sample 107 is placed on the microscope stage 106 and positioned such that a target spot 109 is aligned with an optical axis including the objective lens 104 (FIG. 1). This initial alignment can be performed manually through the observation head 110 (FIG. 1), automatically using the controller 116, or through a combination of a course manual adjustment followed by a fine controller 116 adjustments. For test samples including a regular array of target spots 109, the test sample 107 is preferably aligned once (e.g., for one target spot 109) and then re-positioned to test additional target spots 109 of the sample 107 using preprogrammed offset adjustments of the stage 106.

Once the target spot 109 is aligned with the optical axis, the system 100 acquires a sample image of the target spot 109 using the CCD camera 112 (FIG. 1). For the exemplary fluorescence IHC system, the sample image is obtained for a chosen wavelength band or channel of interest using a respective one of the filter blocks 108 (FIG. 1) corresponding to the channel. The calibration cube 130 (FIG. 2) is selected through rotation of the turret 115 (FIG. 1). A reference image of the excitation source is also obtained using the calibration cube 130 for a determination of the excitation source intensity. Additional filter cubes 108 can be used to obtain additional sample images through different channels, as required. The particular order in which the channels and excitation source samples are obtained can be varied, provided that the one or more channel images are related to the excitation source reference image (e.g., taken at approximately the same time). Such a relationship can be accomplished by forming a composite image of the multiple images, or otherwise labeling the images to reflect their relationship.

The sample and reference images can be sent from the camera 112 to the controller 116 or separate image analyzer for later analysis and correction at step 240. Image analysis can include calculating AQUA scores for each of the different channels. One or more of the correction factors (CC, OP, LS) are applied at step 250 to obtain corrected or standardized results. The standardized output data for the particular target spot 109 of the test sample 107 is provided at step 260. The test sample procedure 200 can be repeated for additional target spots 109 of the same test sample 107. The test sample procedure 200 can also be repeated for one or more additional test samples 107 using the same correction factors obtained at step 220.

Figure 9:
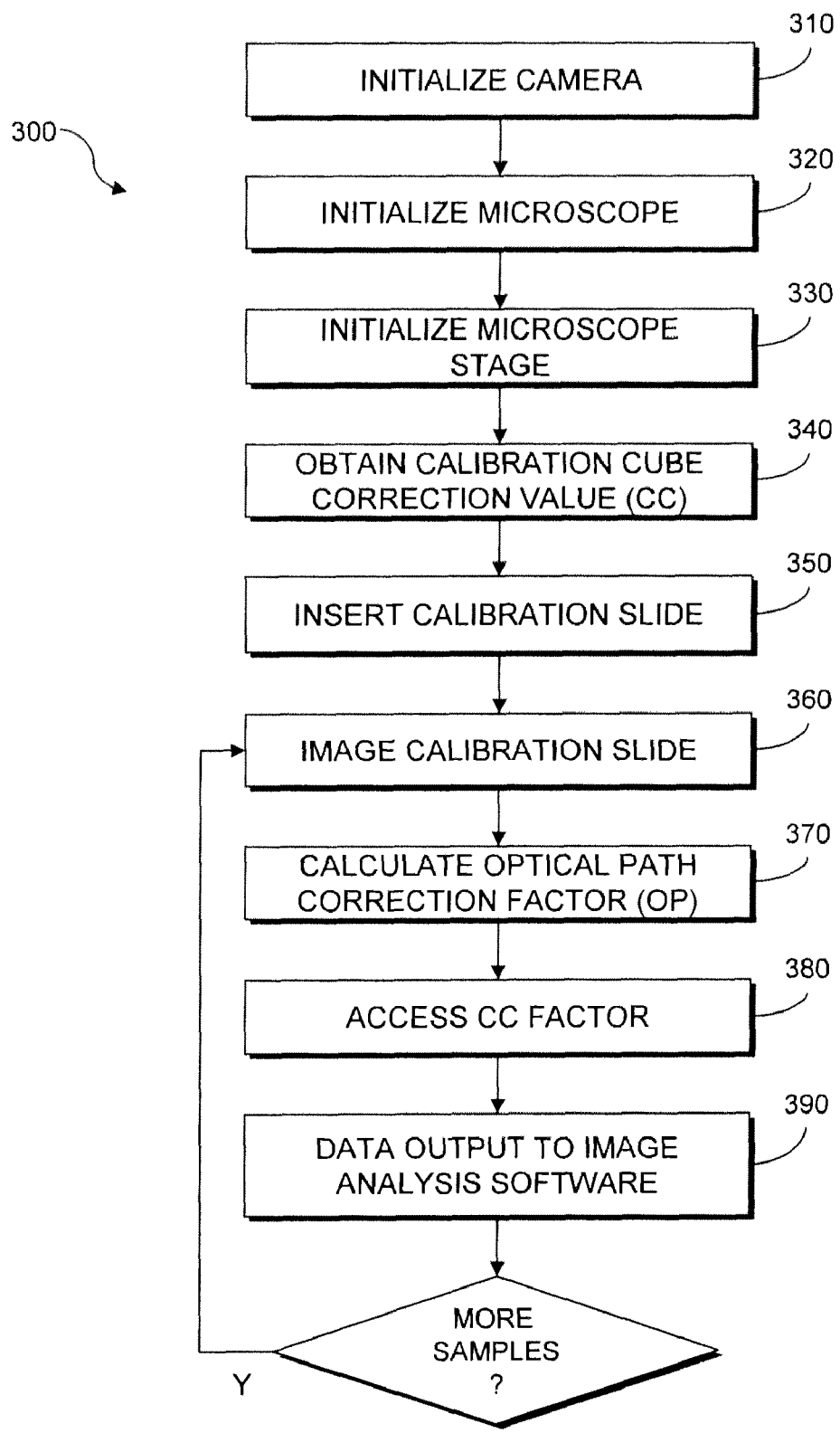
FIG. 9 shows a flow diagram of a process for obtaining correction factors used in the standardization of qualitative analysis results of FIG. 8.

In more detail, an exemplary flow diagram of an initialization procedure 300 for obtaining correction factors used in the standardization of qualitative analysis results is shown in FIG. 9. The camera 112 (FIG. 1) and microscope are respectively initialized at steps 310 and 320. These steps may be conducted sequentially or in parallel. Providers of the camera 112 and microscope system 110 typically define these initialization steps 310, 320 in the form of an initialization procedure. One or more of the initialization procedures may be automated and occur as part of a power on cycle.

Next, the microscope stage 106 (FIG. 1) is initialized at step 330 to allow for proper alignment of test samples during test. In some embodiments, a calibration slide including a target sample is placed onto the microscope stage 106 at step 350. The calibration slide is selected to provide a known response during characterization of the optical path, as may be performed at the time of manufacture, or servicing of the microscopy system. An image of the calibration slide is obtained at step 360 and an optical path correction factor, or machine intrinsic factor (OP) is determined at step 370. The machine intrinsic factor can be stored for later use during normal operation to remove optical path variability between different microscopy systems. This step of determining the machined intrinsic factor includes obtaining a sample image of the excitation source using the calibration cube 130 (FIG. 2) to determine intensity of the calibration source. Preferably, the excitation source sample is obtained immediately adjacent to the step of obtaining an image of the calibration slide to minimize the likelihood of intensity variation between samples.

Next, the calibration cube correction factor (CC) is accessed at step 380. This value can be stored into the system or manually entered during the preliminary initialization process 300. This value can be obtained by comparing results obtained from the calibration cube 130 with results obtained using a universally standard calibration cube and formulating a ratio of the results. Similar to the optical path correction factor, determination of the calibration cube correction factor need not be repeated during normal use. As described above, the calibration cube is preferably constructed to reduce or eliminate any variability in its performance over time. Thus, an initial determination of the calibration cube correction factor can be obtained at the time of its manufacture (the factory holds a "gold" standard calibration cube used in comparison to manufactured calibration cubes to obtain the correction factor). The resulting correction factor can be marked on the calibration cube itself and/or provided to the processor for later use during correction of sampled images. Once obtained, the machine intrinsic factor (OP) and calibration cube correction factor (CC) are output to image analysis software at step 390 (e.g., read from memory locations containing pre-stored values). This can include forwarding the factors (OP, CC) to the controller 116 or separate image analyzer for storage and later use to standardize images of actual test samples. Steps 360 and 380 can be repeated for different channels of the same calibration slide and output separately to the image analysis software at step 390. Thus, the machine intrinsic factor (OP) is determined and retained on a per-channel basis and stored separately for later analysis of test samples on a per-channel basis using the appropriate machine intrinsic factor. In some embodiments, steps 360, 380, and 390 can be repeated for the same channel to allow for statistical determination of the machine intrinsic factor. Thus, multiple results for each channel can be obtained and used to formulate an average result that is stored for later use.

An equation provided below (EQ. 1) was used to standardize results obtained for each system 100. The calibration cube correction factor (CC) and machine intrinsic factors (OP) were determined for each system and stored for later use in manipulating test results. Next, standard quantitative results (specimen quantitative score$_{raw}$) were obtained for a particular specimen, or sample under test. Through a correction process, the raw quantitative score is multiplied by the various correction factors, to yield a normalized quantitative result suitable for comparison among different systems.

$$\text{Specimen Quantitative Score}_{normalized} = (\text{specimen quantitative score}_{raw})*(CC)*(OP)*(100,000/LS) \quad (\text{Eq. 1})$$

The above equation provided a direct multiplicative standardization scheme using two constants which were intrinsic to the calibration cube and microscopy system (CC and OP). Both of these factors were scaled as described above, such that data were standardized to an ideal system. Thus, a calibration cube approximating the "gold standard" would result in a CC approaching 1.0. Similarly, an optical path approaching a standard reference optical path would also approach 1.0. In the case of the light source fluctuation factor (LS), an empirically derived value of 100,000 was used to define an ideal intensity value for this factor. This value of 100,000 was then divided by the particular LS value obtained during each measurement. Table 3 shows the resulting standardization correction factor obtained for five different instruments.

TABLE 3

Standardization Factor for Five Instruments

| Instrument | Correction: (CC) * (OP) * (100,000) |
|---|---|
| 1 | 97446 |
| 2 | 116702 |
| 3 | 172794 |
| 4 | 88300 |
| 5 | 132000 |

Figure 10:
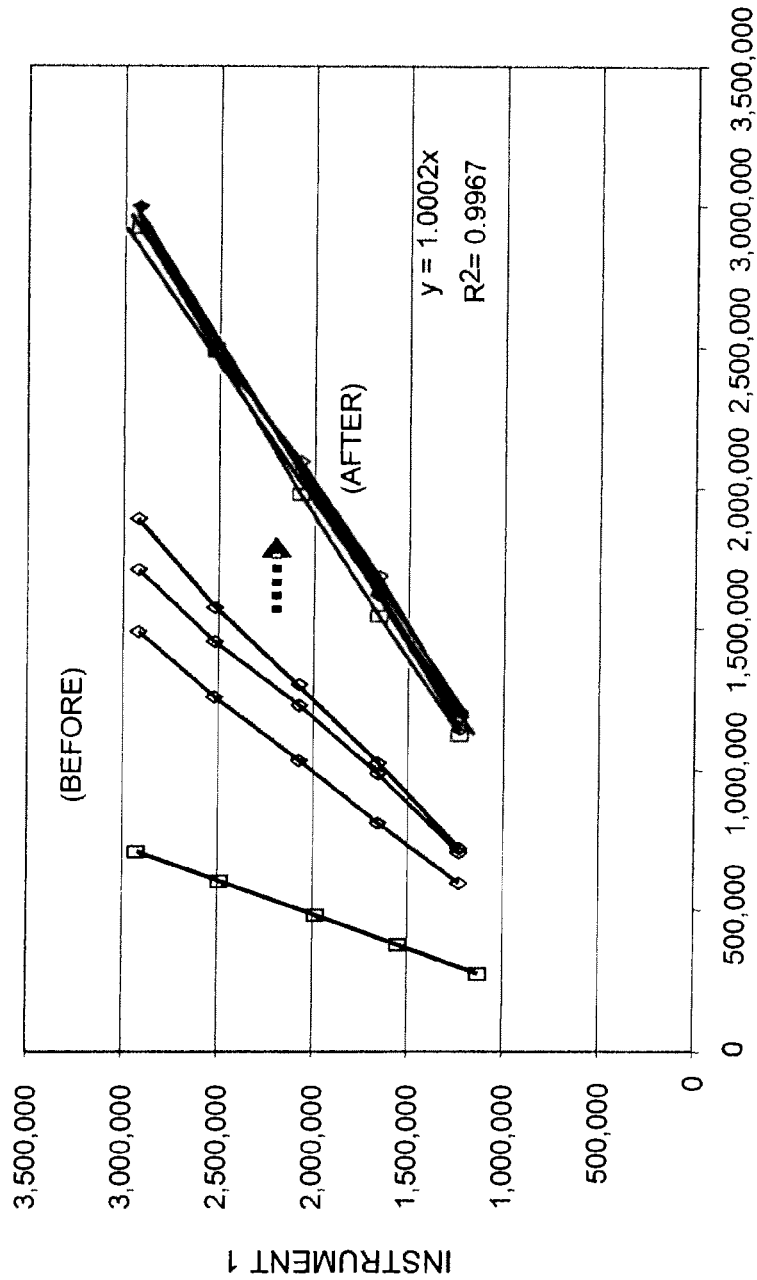
FIG. 10 shows comparative results obtained using different microscope systems without and with correction accordance with principles of the present invention.

Using the correction factors described herein (CC, OP, LS), the quantitative data obtained using the five different instruments were all correlated to instrument 1. The correlation results are illustrated graphically in FIG. 10. As can be seen from the figure, before correction, the correlations of each instrument to instrument 1 result in non-overlapping curves varying substantially from instrument 1. After application of the correction factors, however, the corrected correlation curves for all five instruments to instrument 1 overlap substantially, demonstrating a high degree of correlation to instrument 1 and to each other.

EXAMPLE: In use, a test sample can include a tissue microarray (TMA) including a matrix of tissue samples on a single microscope slide. For example, a 36 spot tissue microarray including breast cancer tissue samples, BT474, MCF7, T47D cell line control samples was stained. The staining protocol involved deparafinization in xylene, rehydration through a series of decreasing amounts of ethanol to pure water, and antigen retrieval in Tris EDTA. After endogenous peroxidase blocking and blocking with background sniper, HER 2, (CB11) and cytokeratin (Rabbit, Dako) primary antibodies were applied and rinsed off after 1 hour. Dako Envision anti-mouse and Invitrogen alexa 555 GAR were then applied. After extensive washing, cy 5 tyramide was applied. The slides were then washed in TBS/Tween 20. Finally, a mounting media with Dapi was applied and the slides were dried.

The fluorescent intensity of staining for HER2 and resulting AQUA score were collected for each tissue spot of the tissue micro array using instruments 1 and 2 included in Table 3.

Scores were standardized using Eq. 2 and Eq. 3 below.

$$\text{Quantitative Score}_{normalized} = (\text{Quantitative Score}_{raw\ Instrument\ 1}/LS_{Instrument\ 1})*97{,}446. \quad (\text{Eq. 2})$$

$$\text{Quantitative Score}_{normalized} = (\text{Quantitative Score}_{raw\ Instrument\ 2}/LS_{Instrument\ 2})*116{,}702. \quad (\text{Eq. 3})$$

Figure 11B:
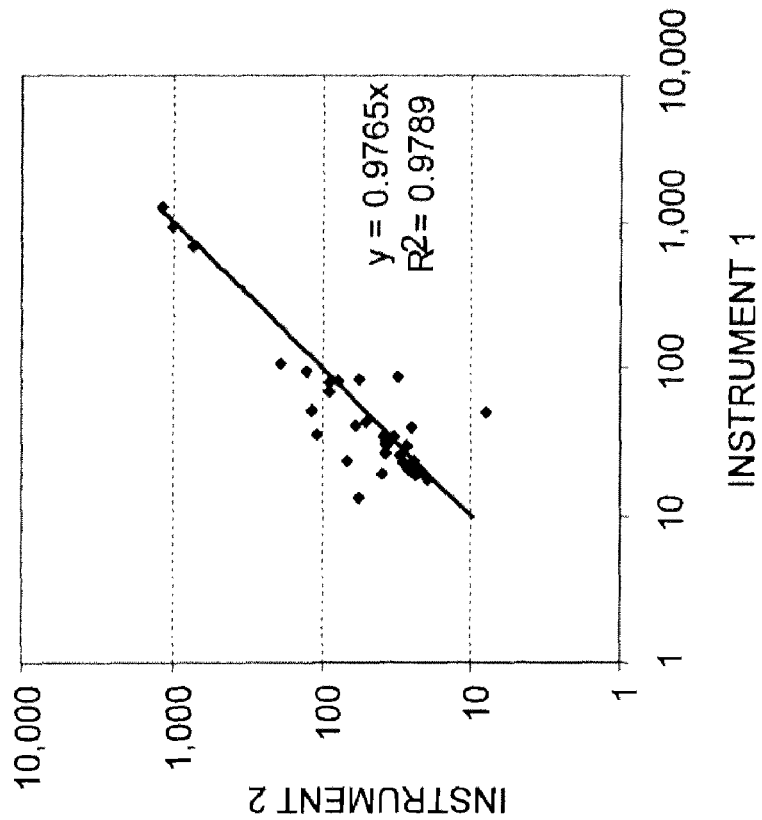
FIGS. 11A and 11B show comparison of uncorrected and corrected sample data obtained in accordance with principles of the present invention.
Figure 11A:
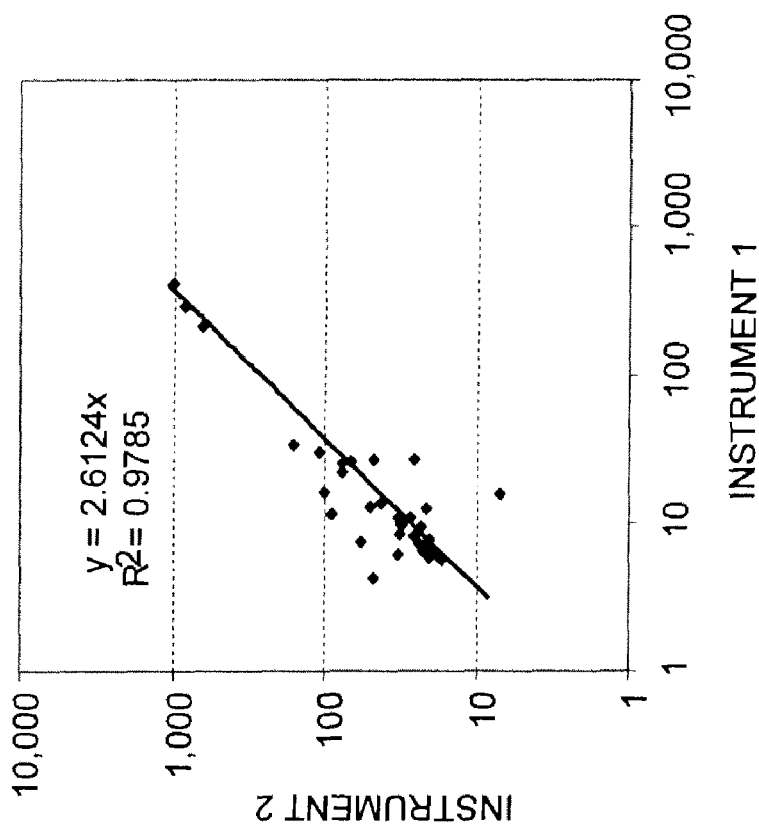

AQUA scores for each sample in the 36 spot tissue micro array were acquired using two different instruments. The raw AQUA scores shown in FIG. 11A and the normalized AQUA scores shown in FIG. 11B from the 36 spot tissue micro array, acquired on two instruments were graphed in scatter plot format. The results show a slope of the regression line of the correlation coefficient of 2.6:1 between the two instruments using the raw scores. Using the standardization methods of the invention, a slope of the regression line of the correlation coefficients of 0.98:1 between the two instruments was achieved showing that the distribution of scores are not effected by standardization.

Non-parametric Spearman's rho statistical analysis was used to describe the ranking relationship before and after standardization. The analysis was performed using the AQUA score data set obtained from two instruments. Rank-orders are assigned from smallest original value (=rank 1) to highest original value for each AQUA score. The correlation coefficient and the P-Value were calculated for the standardized and the non-standardized (raw) datasets. The rank order of the data was unaffected by standardization (Table 4).

TABLE 4

Spearman Rho analysis

|  | Normalized Data | Raw Data |
|---|---|---|
| Rho: | 0.72 | 0.721 |
| P-Value: | <0.0001 | <0.0001 |

EXAMPLE: The same 36 spot stained tissue micro array described in the above example was acquired and scored on five different instruments.

The results indicated that the percent coefficient of variation (% CV) of the raw AQUA scores and the standardized AQUA scores for each tissue micro array tissue spot acquired on the five different instruments shows significantly better % CV is achieved by standardization by the methods of the invention.

Tables 5 and 6 are compilations of the slope of the regression line of the correlation coefficient generated with a single slide run on the five instruments. Correlations based on raw AQUA scores are shown in Table 5 and those based on standardized AQUA scores are shown in Table 6. This comparison was done with numbers generated from validated images.

TABLE 5

Raw data

| Raw Data | Instrument 1 | Instrument 2 | Instrument 3 | Instrument 4 | Instrument 5 |
|---|---|---|---|---|---|
| Instrument 1 | N/A | 0.44x | 2.55x | 1.68x | 2.51x |
| Instrument 2 | 0.44x | N/A | 0.17x | 3.85x | 5.76x |
| Instrument 3 | 2.55x | 0.17x | N/A | 0.66c | 0.98x |
| Instrument 4 | 1.68x | 3.85x | 0.66x | N/A | 1.50x |
| Instrument 5 | 2.51x | 5.76x | 0.98x | 1.50x | N/A |

TABLE 6

Standardized data

| Normalized Data | Instrument 1 | Instrument 2 | Instrument 3 | Instrument 4 | Instrument 5 |
|---|---|---|---|---|---|
| Instrument 1 | N/A | 0.88x | 0.95x | 1.09x | 0.89x |
| Instrument 2 | 0.88x | N/A | 0.92x | 1.24x | 1.00x |

TABLE 6-continued

Standardized data

| Normalized Data | Instrument 1 | Instrument 2 | Instrument 3 | Instrument 4 | Instrument 5 |
|---|---|---|---|---|---|
| Instrument 3 | 0.95x | 0.92x | N/A | 1.14x | 0.93x |
| Instrument 4 | 1.09x | 1.24x | 1.14x | N/A | 1.23x |
| Instrument 5 | 0.89x | 1.00x | 0.93x | 1.23x | N/A |

The percent coefficient of variation (% CV) of the raw AQUA® scores and the standardized AQUA scores for each tissue micro array tissue spot acquired on five instruments shows significantly better % CV is achieved by standardization by the methods of the invention.

Figure 12A:
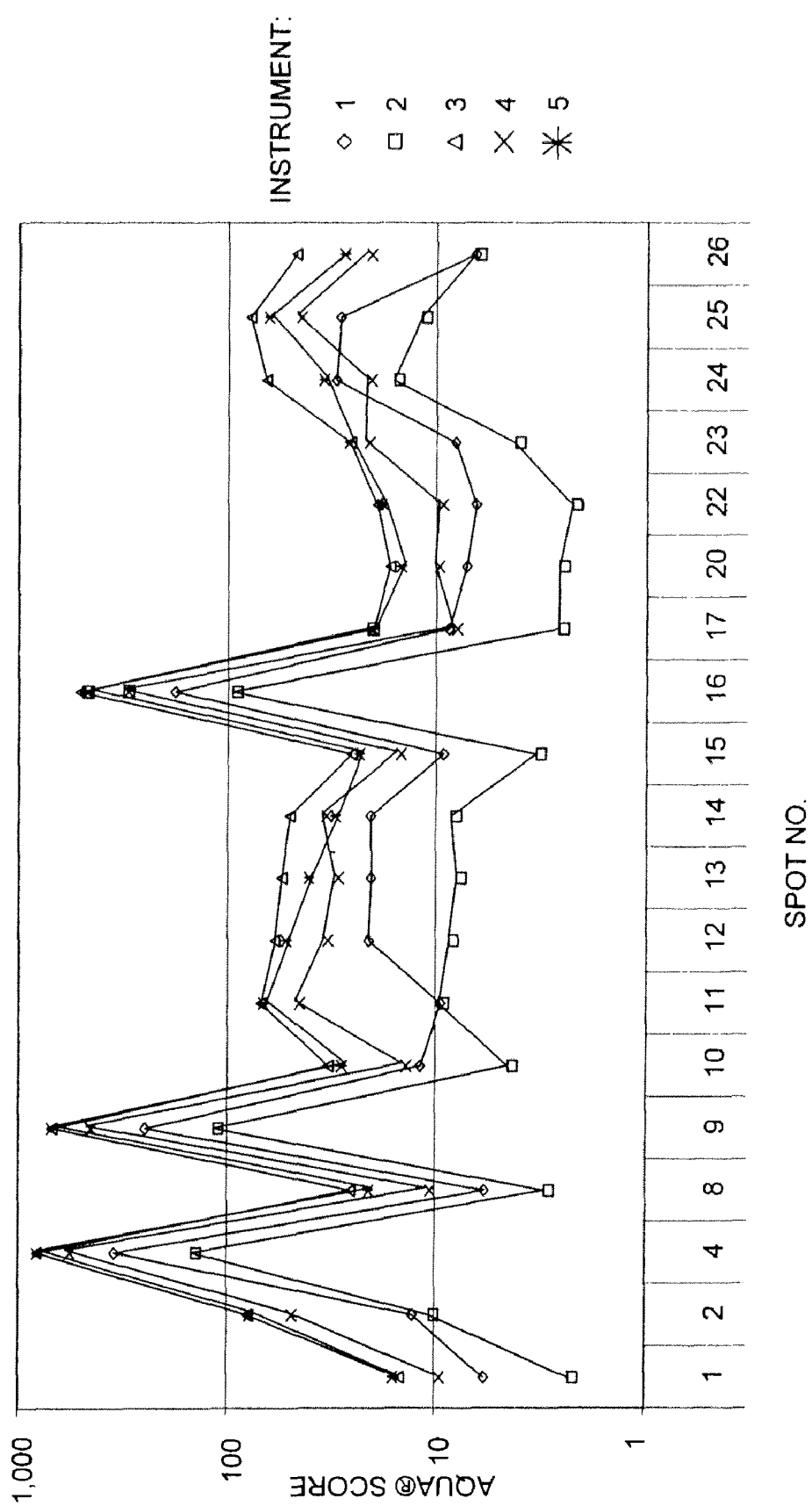
FIG. 12A shows exemplary qualitative analysis results obtained from the same sample using different microscope systems without standardization.
Figure 12B:
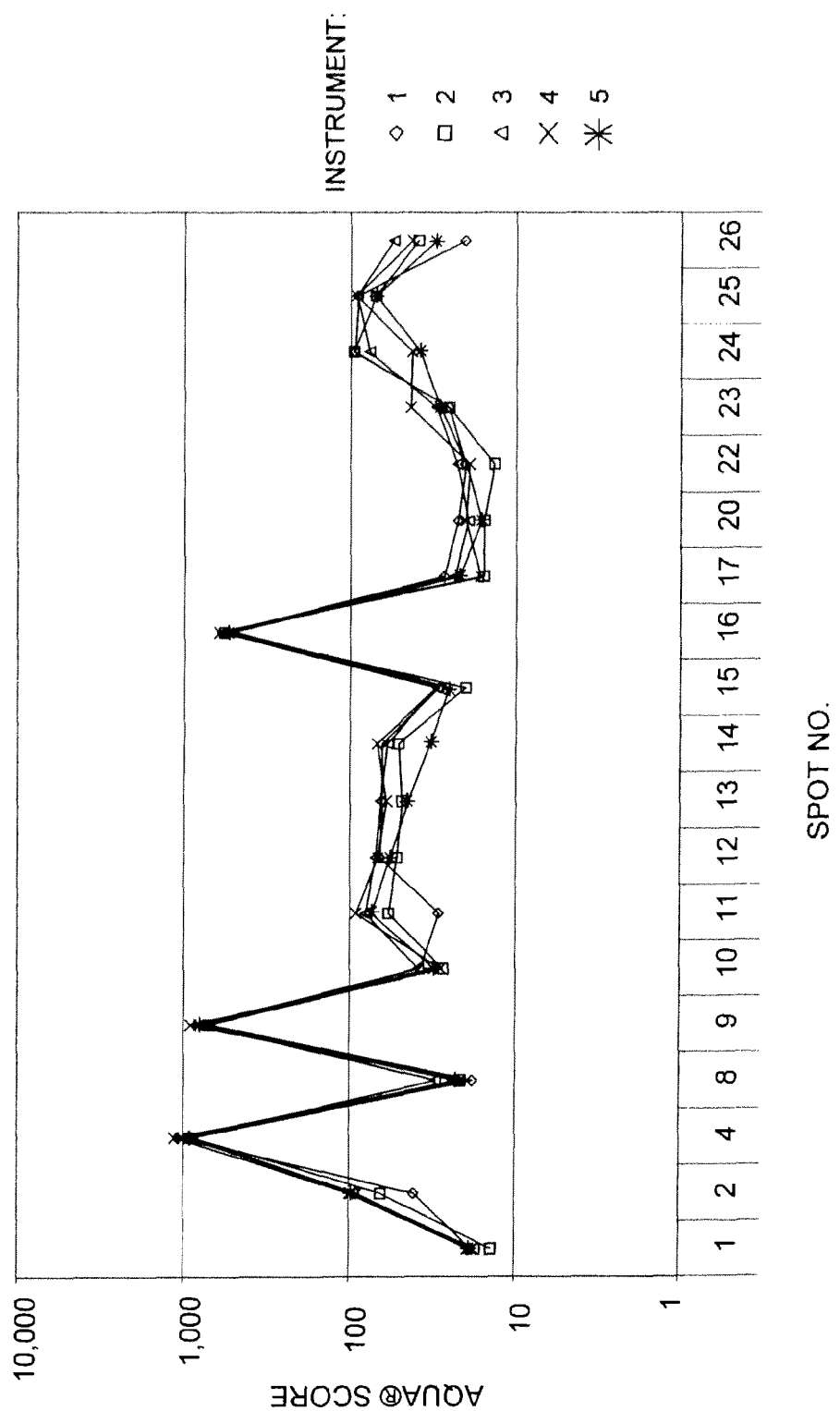
FIG. 12B shows correction of the qualitative results of FIG. 12A in accordance with principles of the present invention.

The mean AQUA scores for HER2 staining of 26 validated tissue micro array spots of the 36 are shown in FIG. 12A and FIG. 12B. While trends or comparisons across the 36 samples are similar on each instrument, score variance for each individual sample have an average CV of approximately 60% from instrument to instrument. In comparison the mean scores obtained on each of the same 5 instruments, once standardized FIG. 12B are more consistent, with an average CV of approximately 20%.

An analysis of variance (ANOVA) test for significant differences between means before and after standardization using the null hypothesis that the instruments are identical produces a significant p value <0.05 thus rejecting the null hypothesis indicating the marginal mean scores collected on multiple instruments are different. After standardization the p value of >0.05 indicates that marginal mean scores collected on multiple instruments is now not significantly different.

Although the exemplary embodiments relate primarily to fluorescent microcopy, the invention is broadly applicable to optical microscopes in general. The techniques of various embodiments apply to correcting for variations in intensity of any light source using a calibration instrument, correcting for calibration instrument variations using offsets to a universally standard calibration instrument, and/or normalizing effects of the optical path through a particular optical microscope system. Thus, various embodiments of the invention can be applied generally with a variety of optical microscopes using incoherent illumination sources, polarized illumination sources, and coherent illumination sources, such as confocal laser scanning microscope systems.

System requirements for an exemplary fluorescent microscopy system are included in Table 7.

TABLE 7

Exemplary Fluorescent Microscopy System Requirements

| Component | Target Specifications | Example |
|---|---|---|
| Microscope | Epi-fluorescence microscope | Olympus BX51 |
| | Stage automation to facilitate image acquisition (optional) | HistoRx PM2000 ™ system (Prior Stage) with associated AQUAsition ™ software |
| | Mercury (Hg) arc fluorescence light source. It is strongly recommended that light sources possess an adjustable iris or safety shutter if light measurements are being made | Exfo X-cite with adjustable iris |
| | Fluorescence filter/channels to accommodate DAPI (UV)/ Cy3/Alexa555, and Cy5/Alexa 647 | No example given |
| | Objectives based on camera resolution described below | Olympus UPLSAPO series objectives |
| Monitoring/Calibration | Standard slide to provide reference for microscope standardization. [Optional] Ability to measure incoming light intensity to microscope (in Watts) | Omega optical fluorescence reference slide (blue; XF900); [Optional] Exfo NIST traceable radiometer (part no. P010-00200) |
| Camera | CCD monochromatic capability, 8 or 12 bit resolution | Optronics QuantiFire XI CCD camera (2048 × 2048 pixels, 7.4 μM/pixel) coupled with Olympus UPLSAPO 20X objective |
| Field of view size (Camera/Objective combination) | Pixel size objective magnification combination which provides field-of-view size between 671 μM and 888 μM. Field of view size calculation (for cameras with rectangular CCDs, values must be calculated for both dimensions): (CCD pixel size) * (number of CCD pixels)/(objective magnification) | Calculation for example hardware: (7.4 μM) * (2048)/ (20) = 758 μM field of view |
| Acquisition exposure | Images must be acquired at optimal exposure settings such that image pixels are not saturated, yet intensity dynamic range is maximized | — |
| Computer, monitor, keyboard, mouse | Windows XP Professional (SPS) equipped with a DVD-ROM drive. 20" monitor for image visualization. | — |

It will be realized by one skilled in the art, that one or more of the steps of obtaining the various correction factors: CC, LS, OP can be obtained automatically or at least semi-automatically with the assistance of a processor, such as computer. Alternatively or in addition, one or more of the steps used in determining standardized target image data and/or a quantitative measure therefrom can be automated, for example, with the assistance of a processor. For example, such a processor can be implemented by a computer executing pre-programmed instructions. Such automation facilitates elimination of the inherent variability of pathologist-based scoring.

While this invention has been particularly shown and described with references to preferred embodiments thereof, it should be apparent that unique operational features have been described. Although particular embodiments have been disclosed herein in detail, this has been done by way of example for purposes of illustration only, and is not intended to be limiting with respect to the scope of the appended claims which follow. In particular, it is contemplated by the inventors that various substitutions, alterations, and modifications may be made to the invention without departing from the spirit and scope of the invention encompassed in the appended claims. For instance, the choice of materials for the filter, the ordering of measurement and analysis steps, and the configuration of the filters, stage, and excitation source employed is believed to be matter of routine for a person of ordinary skill in the art with knowledge of the embodiments described herein.

What is claimed is:

1. A calibration instrument for sampling illumination of an excitation light source of a microscopy system, comprising:
    a calibration surface positioned along an optical path to substantially uniformly scatter illumination from the excitation light source toward a detection portion of the microscopy system;
    a dichromatic mirror positioned to reflect illumination from the excitation light source along an optical path through an objective toward a target sample and to transmit at least a portion of illumination from the target sample toward a detection portion of the microscopy system, wherein the calibration surface temporarily blocks the optical path between the dichromatic mirror and the objective during calibration and scatters a substantial portion of the reflected excitation light through the dichromatic mirror toward the detector; and
    a housing configured to retain the dichromatic mirror and the calibration surface in a fixed relation with respect to each other, wherein the housing is adapted for placement within an interchangeable filter selection mechanism.

2. The calibration instrument of claim 1, wherein the calibration surface is opaque.

3. The calibration instrument of claim 2, wherein the opaque calibration surface comprises filter paper.

4. The calibration instrument of claim 2, wherein the opaque calibration surface comprises a substantially rigid surface.

5. The calibration instrument of claim 4, wherein the substantially rigid surface comprises a ceramic surface.

6. The calibration instrument of claim 1, further comprising at least one neutral filter positioned to attenuate at least one of the illumination from the excitation light source and the illumination from the target sample, and wherein the housing is further configured to retain the dichromatic mirror, the at least one neutral filter, and the calibration element in fixed relation with respect to each other.

* * * * *